United States Patent [19]

Yoshimoto et al.

[11] 4,247,548
[45] Jan. 27, 1981

[54] 7α-METHOXYCEPHALOSPORIN DERIVATIVES AND THEIR PHARMACEUTICAL COMPOSITIONS HAVING ANTIBACTERIAL ACTIVITY

[75] Inventors: Masafumi Yoshimoto; Hachio Miyazawa; Takuzo Nishimura; Akiko Ando; Norio Nakamura; Hideo Nakao, all of Hiromachi, Japan

[73] Assignee: Sankyo Company Limited, Tokyo, Japan

[21] Appl. No.: 28,707

[22] Filed: Apr. 10, 1979

[30] Foreign Application Priority Data

Apr. 11, 1978 [JP] Japan ................................. 53-42360

[51] Int. Cl.³ ................... A61K 31/545; C07D 501/57
[52] U.S. Cl. ........................................ 424/246; 544/21
[58] Field of Search ............................ 544/21; 424/246

[56] References Cited

U.S. PATENT DOCUMENTS

| | | | |
|---|---|---|---|
| 3,891,635 | 6/1975 | Henniger et al. | 424/246 X |
| 3,960,845 | 1/1976 | Hiraoka et al. | 424/246 X |
| 4,007,177 | 2/1977 | Nakao et al. | 544/21 |
| 4,010,264 | 3/1977 | Henniger et al. | 424/246 |
| 4,051,129 | 9/1977 | Shimizu et al. | 544/21 |

FOREIGN PATENT DOCUMENTS

| | | | |
|---|---|---|---|
| 2409949 | 9/1974 | Fed. Rep. of Germany | 544/27 |
| 1348984 | 3/1974 | United Kingdom | 544/21 |

Primary Examiner—Donald G. Daus
Assistant Examiner—Diana G. Rivers
Attorney, Agent, or Firm—Frishauf, Holtz, Goodman & Woodward

[57] ABSTRACT

7α-Methoxycephalosporin derivatives of general formula (I):

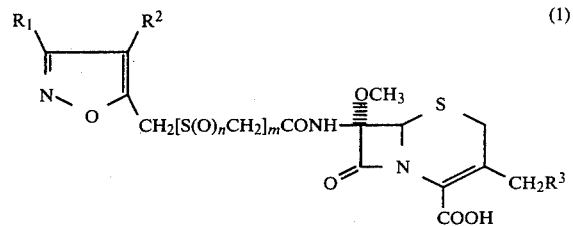

wherein:

$R^1$ represents a hydroxy group; a $C_1$–$C_4$ alkoxy group; a $C_2$–$C_5$ aliphatic acyloxy group; a benzoyloxy group which is unsubstituted or has one or more $C_1$–$C_4$ alkyl, $C_1$–$C_4$ alkoxy, nitro or halogen substituents; a benzenesulphonyloxy group which is unsubstituted or has one or more $C_1$–$C_4$ alkyl substituents; or a $C_1$–$C_3$ alkanesulphonyloxy group which is unsubstituted or has one or more $C_1$–$C_3$ alkoxy, cyano, nitro, halogen or $C_2$–$C_4$ alkoxycarbonyl substituents;

$R^2$ represents a hydrogen atom, a $C_1$–$C_4$ alkyl group, a halogen atom, a carboxyl group, a $C_2$–$C_5$ alkoxycarbonyl group, a carbamoyl group, an alkylcarbamoyl group in which the alkyl moiety has from 1 to 3 carbon atoms, a di($C_1$–$C_3$ alkyl)carbamoyl group or a cyano group;

$R^3$ represents a hydrogen atom; an acetoxy group; a carbamoyloxy group; or a tetrazolylthio, thiadiazolylthio or oxadiazolylthio group which is unsubstituted or has one or more $C_1$–$C_3$ alkyl, sulphomethyl or di($C_1$ or $C_2$ alkyl)amino($C_1$–$C_3$ alkyl) substituents;

m is 0 or 1; and
n is 0 or 2 exhibit potent antibacterial activity and are thus useful as medicines. The derivatives can be prepared by reacting the corresponding 7α-methoxycephalosporin derivative having an amino group at the 7β-position with an acid halide corresponding to the substituted acetyl group which it is desired to attach to the amino group at the 7β-position or by reacting Cephamycin C with the same acid halide.

17 Claims, No Drawings

# 7α-METHOXYCEPHALOSPORIN DERIVATIVES AND THEIR PHARMACEUTICAL COMPOSITIONS HAVING ANTIBACTERIAL ACTIVITY

BACKGROUND OF THE INVENTION

The present invention relates to a novel series of 7α-methoxycephalosporin derivatives, to salts and esters thereof, to the use of the compounds as pharmaceuticals and to novel methods for the preparation of these compounds.

Although the antibacterial activity of the original member of the cephalosporin series, cephalosporin is only moderate, numerous cephalosporin derivatives have been prepared and found to be excellent antibacterial agents and some of them have found practical use in chemotherapy. Recently, the class of cephalosporins having a methoxy group at the 7α-position have been subject to increasing investigation. Characteristically, these 7α-methoxycephalosporins have stronger antibacterial activity against cephalosporin-resistant bacteria, Serratia and indole-positive Proteus strains than the corresponding 7αH-cehalosporins. On the other hand, the activities of these 7α-methoxycephalosporins against other bacteria are generally equivalent to or perhaps even less than the activities of the corresponding 7αH-cephalosporins.

We have now discovered a series of 7α-methoxycephalosporin derivatives which surprisingly have stronger antibacterial activity against most bacteria than the corresponding known compounds having a hydrogen atom at their 7α-position; these known compounds are described, for example, in United Kingdom Pat. No. 1,464,377.

BRIEF SUMMARY OF INVENTION

It is therefore an object of the present invention to provide a novel series of 7α-methoxycephalosporin derivatives.

It is a further object of the invention to provide pharmaceutical compositions containing one or more of these 7α-methoxycephalosporin derivatives as active agent.

It is a still further object of the invention to provide methods for preparing the new 7α-methoxycephalosporin derivatives.

The new 7α-methoxycephalosporin derivatives of the present invention are those compounds of formula (I):

$$R^1\diagdown\phantom{xxx}R^2 \quad (I)$$

(structure with $CH_2[S(O)_nCH_2]_mCONH$—, $OCH_3$, S, N, $CH_2R^3$, COOH)

wherein:
$R^1$ represents a hydroxy group; a $C_1-C_4$ alkoxy group; a $C_1-C_4$ alkoxy group; a $C_2-C_5$ aliphatic acyloxy group; a benzoyloxy group which is unsubstituted or has one or more $C_1-C_4$ alkyl, $C_1-C_4$ alkoxy, nitro or halogen substituents; a benzenesulphonyloxy group which is unsubstituted or has one or more $C_1-C_4$ alkyl substituents; or a $C_1-C_3$ alkanesulphonyloxy group which is unsubstituted or has one or more $C_1-C_3$ alkoxy, cyano, nitro, halogen or $C_2-C_4$ alkoxycarbonyl substituents;

$R^2$ represents a hydrogen atom, a $C_1-C_4$ alkyl group, a halogen atom, a carboxyl group, a $C_2-C_5$ alkoxycarbonyl group, a carbamoyl group, an alkylcarbamoyl group having from 1 to 3 carbon atoms in the alkyl moiety, a di($C_1-C_3$ alkyl)carbamoyl group or a cyano group;

$R^3$ represents a hydrogen atom; an acetoxy group; a carbamoyloxy group; or a tetrazolylthio, thiadiazolylthio or oxadiazolylthio group which is unsubstituted or has one or more $C_1-C_3$ alkyl, sulphomethyl or di($C_1$ or $C_2$ alkyl)-amino($C_1-C_3$ alkyl) substituents;

m is 0 or 1; and
n is 0 or 2 and salts and esters thereof.

DETAILED DESCRIPTION OF INVENTION

Within the new compounds of formula (I) preferred classes of compounds are those represented by general formulae (II) and (III):

(structure II with $R^1$, $R^2$, $CH_2S(O)_nCH_2CONH$—, $OCH_3$, S, N, $CH_2R^3$, COOH)

in which $R^1$, $R^2$, $R^3$ and n are as defined above;

(structure III with $R^1$, $R^4$, $CH_2CONH$—, $OCH_3$, S, N, $CH_2R^3$, COOH)

in which $R^1$ and $R^3$ are as defined above and $R^4$ represents a hydrogen atom, a $C_1-C_4$ alkyl group or a halogen atom.

In the above formulae, where $R^1$ represents an alkoxy group, this has from 1 to 4 carbon atoms and may be a straight or branched chain alkoxy group. Examples include the methoxy, ethoxy, n-propoxy, isopropoxy, n-butoxy and isobutoxy groups.

Where $R^1$ represents an aliphatic acyloxy group, this has from 2 to 5 carbon atoms and may be a straight or branched chain group. Examples include the acetoxy, propionyloxy, butyryloxy, isobutyryloxy and pivaloyloxy groups.

Where $R^1$ represents a benzoyloxy group, this may be unsubstituted or may have one or more $C_1-C_4$ alkyl (e.g. methyl, ethyl, n-propyl or isopropyl), $C_1-C_4$ alkoxy (e.g. methoxy, ethoxy, n-propoxy or isopropoxy) nitro or halogen (e.g. chlorine or bromine) substituents.

Where $R^1$ represents a benzenesulphonyloxy group, this may be unsubstituted, or may have one or more $C_1-C_4$ alkyl (e.g. methyl, ethyl, n-propyl or isopropyl) substituents; a particularly preferred such substituted benzenesulphonyloxy group is the p-toluenesulphonyloxy group.

Where $R^1$ represents a $C_1$–$C_3$ alkanesulphonyloxy group, this may be unsubstituted or may have one or more $C_1$–$C_3$ alkoxy (e.g. methoxy or ethoxy), cyano, nitro, halogen (e.g. chlorine or bromine) or $C_2$–$C_4$ alkoxycarbonyl (e.g. methoxycarbonyl or ethoxycarbonyl) substituents. Examples of such groups include the methanesulphonyloxy, ethanesulphonyloxy, n-propanesulfonyloxy, methoxymethanesulphonyloxy, cyanomethanesulfonyloxy, 2-nitroethanesulphonyloxy, 2-chloroethanesulfonyloxy or ethoxycarbonylmethanesulphonyloxy groups.

Where $R^2$ represents a $C_1$–$C_4$ alkyl group, this may be a straight or branched chain group, for example methyl, ethyl, n-propyl, isopropyl, n-butyl or isobutyl.

Where $R^2$ represents a halogen atom, this is preferably a chlorine or a bromine atom.

Where $R^2$ represents an alkoxycarbonyl group, this may be a straight or branched chain group and should have a total of from 2 to 5 carbon atoms. Such groups include the methoxycarbonyl, ethoxycarbonyl, n-propoxycarbonyl, isopropoxycarbonyl, n-butoxycarbonyl and isobutoxycarbonyl groups.

Where $R^2$ represents a carbamoyl group, this may be unsubstituted or may have one or two $C_1$–$C_3$ alkyl substituents, which may be straight or branched chain groups. Examples include the carbamoyl group itself and the methylcarbamoyl, ethylcarbamoyl, n-propylcarbamoyl, isopropylcarbamoyl, dimethylcarbamoyl, diethylcarbamoyl, di-n-propylcarbamoyl and diisopropylcarbamoyl groups.

$R^3$ may represent a hydrogen atom, an acetoxy group, a carbamoyloxy group or a tetrazolylthio, thiadiazolylthio or oxadiazolylthio group, these heterocyclic groups being unsubstituted or having one or more $C_1$–$C_3$ alkyl (e.g. methyl, ethyl, n-propyl or isopropyl), sulphomethyl or di($C_1$ or $C_2$ alkyl)amino($C_1$–$C_3$ alkyl) (e.g. dimethylaminoethyl or diethylaminopropyl) substituents.

Within the compounds of the invention, a preferred group of compounds is those in which:

$R^1$ represents a hydroxy group, an unsubstituted benzoyloxy group or a methanesulphonyloxy group;

$R^2$ represents a hydrogen atom, a $C_1$–$C_3$ alkyl group, a halogen atom, a $C_2$–$C_4$ alkoxycarbonyl group, a carbamoyl group, a ($C_1$–$C_3$ alkyl)carbamoyl group, a di($C_1$–$C_3$ alkyl)carbamoyl group or a cyano group;

$R^3$ represents a $C_1$–$C_3$ alkyl-substituted tetrazolylthio group;

m is 0 or 1; and where m is 1, n is 2.

A more preferred group of compounds is those in which:

$R^1$ represents a hydroxy group, an unsubstituted benzoyloxy group or a methanesulphonyloxy group;

$R^2$ represents a hydrogen atom, a halogen atom or a $C_2$–$C_4$ alkoxycarbonyl group;

$R^3$ represents a methyl- substituted tetrazolylthio group;

m is 0 or 1; and when m is 1, n is 2.

Examples of compounds of the invention are given in the following list; the compounds are hereinafter identified by the numbers assigned to them in this list.

1. 7β-[(3-Benzoyloxyisoxazol-5-yl)acetamido]-7α-methoxy-3-(1-methyl-1H-tetrazol-5-yl)thiomethyl-3-cephem-4-carboxylic acid.

2. 7β-[(3-Hydroxyisoxazol-5-yl)acetamido]-7α-methoxy-3-(1-methyl-1H-tetrazol-5-yl)thiomethyl-3-cephem-4-carboxylic acid.

3. 7α-Methoxy-7β-[(3-methoxyisoxazol-5-yl)acetamido]-3-(1-methyl-1H-tetrazol-5-yl)thiomethyl-3-cephem-4-carboxylic acid.

4. 3-Acetoxymethyl-7β-[(3-benzoyloxyisoxazol-5-yl)acetamido]-7α-methoxy-3-cephem-4-carboxylic acid.

5. 7β-[(3-Hydroxyisoxazol-5-yl)acetamido]-7α-methoxy-3-(5-methyl-1,3,4-thiadiazol-2-yl)thiomethyl-3-cephem-4-carboxylic acid.

6. 7β-[(4-Bromo-3-hydroxyisoxazol-5-yl)acetamido]-7α-methoxy-3-(1-methyl-1H-tetrazol-5-yl)thiomethyl-3-cephem-4-carboxylic acid.

7. 7β-[(4-Chloro-3-hydroxyisoxazol-5-yl)acetamido]-7α-methoxy-3-(1-methyl-1H-tetrazol-5-yl)thiomethyl-3-cephem-4-carboxylic acid.

8. 3-Carbamoyloxymethyl-7α-methoxy-7β-[(3-methoxyisoxazol-5-yl)acetamido]-3-cephem-4-carboxylic acid.

9. 7α-Methoxy-3-(1-methyl-1H-tetrazol-5-yl)thiomethyl-7β-[(3-tosyloxyisoxazol-5-yl)acetamido]-3-cephem-4-carboxylic acid.

10. 7β-[(3-Mesyloxyisoxazol-5-yl)acetamido]-7α-methoxy-3-(1-methyl-1H-tetrazol-5-yl)thiomethyl-3-cephem-4-carboxylic acid.

11. 7β-[(3-Acetoxyisoxazol-5-yl)acetamido]-7α-methoxy-3-(1-methyl-1H-tetrazol-5-yl)thiomethyl-3-cephem-4-carboxylic acid.

12. 7β-[(3-Hydroxy-4-methylisoxazol-5-yl)acetamido]-7α-methoxy-3-(1-methyl-1H-tetrazol-5-yl)thiomethyl-3-cephem-4-carboxylic acid.

13. 7β-[(3-Benzoyloxyisoxazol-5-yl)acetamido]-3-carbamoyloxymethyl-7α-methoxy-3-cephem-4-carboxylic acid.

14. 3-Carbamoyloxymethyl-7β-[(3-mesyloxyisoxazol-5-yl)acetamido]-7α-methoxy-3-cephem-4-carboxylic acid.

15. 7β-[(3-Ethanesulphonyloxyisoxazol-5-yl)acetamido]-7α-methoxy-3-(1-methyl-1H-tetrazol-5-yl)thiomethyl-3-cephem-4-carboxylic acid.

16. 7α-Methoxy-7β-[(3-methoxymethanesulphonyloxyisoxazol-5-yl)acetamido]-3-(1-methyl-1H-tetrazol-5-yl)thiomethyl-3-cephem-4-carboxylic acid.

17. 7β-[(3-Cyanomethanesulphonyloxyisoxazol-5-yl)acetamido]-7α-methoxy-3-(1-methyl-1H-tetrazol-5-yl)thiomethyl-3-cephem-4-carboxylic acid.

18. 7α-Methoxy-3-(1-methyl-1H-tetrazol-5-yl)thiomethyl-7β-[3-(2-nitroethanesulphonyloxy)isoxazol-5-yl]acetamido-3-cephem-4-carboxylic acid.

19. 7β-[(3-Ethoxycarbonylmethanesulphonyloxyisoxazol-5-yl)-acetamido]-7α-methoxy-3-(1-methyl-1H-tetrazol-5-yl)thiomethyl-3-cephem-4-carboxylic acid.

20. 7β-[3-(2-Chloroethanesulphonyloxy)isoxazol-5-yl]acetamido-7α-methoxy-3-(1-methyl-1H-tetrazol-5-yl)thiomethyl-3-cephem-4-carboxylic acid.

21. 7β-[(3-Benzenesulphonyloxyisoxazol-5-yl)acetamido]-7α-methoxy-3-(1-methyl-1H-tetrazol-5-yl)thiomethyl-3-cephem-4-carboxylic acid.

22. 7β-[(4-Chloro-3-mesyloxyisoxazol-5-yl)acetamido]-7α-methoxy-3-(1-methyl-1H-tetrazol-5-yl)thiomethyl-3-cephem-4-carboxylic acid.

23. 7α-Methoxy-3-(1-methyl-1H-tetrazol-5-yl)thiomethyl-7β-[(3-pivaloyloxyisoxazol-5-yl)acetamido]-3-cephem-4-carboxylic acid.

24. 7β-[(4-Bromo-3-mesyloxyisoxazol-5-yl)acetamido]-7α-methoxy-3-(1-methyl-1H-tetrazol-5-yl)thiomethyl-3-cephem-4-carboxylic acid.

25. 7β-[(3-Hydroxy-4-iodoisoxazol-5-yl)acetamido]-7α-methoxy-3-(1-methyl-1H-tetrazol-5-yl)thiomethyl-3-cephem-4-carboxylic acid.

26. 7β-[(4-Iodo-3-mesyloxyisoxazol-5-yl)acetamido]-7α-methoxy-3-(1-methyl-1H-tetrazol-5-yl)thiomethyl-3-cephem-4-carboxylic acid.

27. 7β-[(3-Mesyloxy-4-methoxycarbonylisoxazol-5-yl)acetamido]-7α-methoxy-3-(1-methyl-1H-tetrazol-5-yl)thiomethyl-3-cephem-4-carboxylic acid.

28. 7β-[(3-Hydroxy-4-methoxycarbonylisoxazol-5-yl)acetamido]-7α-methoxy-3-(1-methyl-1H-tetrazol-5-yl)thiomethyl-3-cephem-4-carboxylic acid.

29. 7β-[(4-Carboxy-3-hydroxyisoxazol-5-yl)acetamido]-7α-methoxy-3-(1-methyl-1H-tetrazol-5-yl)thiomethyl-3-cephem-4-carboxylic acid.

30. 3-Acetoxymethyl-7β-[(4-carboxy-3-hydroxyisoxazol-5-yl)-acetamido]-7α-methoxy-3-cephem-4-carboxylic acid.

31. 3-Carbamoyloxymethyl-7β-[(4-carboxy-3-hydroxyisoxazol-5-yl)acetamido]-7α-methoxy-3-cephem-4-carboxylic acid.

32. 7β-[(4-Carboxy-3-hydroxyisoxazol-5-yl)acetamido]-7α-methoxy-3-(5-methyl-1,3,4-thiadiazol-2-yl)thiomethyl-3-cephem-4-carboxylic acid.

33. 7β-[(4-Carbamoyl-3-hydroxyisoxazol-5-yl)acetamido]-7α-methoxy-3-(1-methyl-1H-tetrazol-5-yl)thiomethyl-3-cephem-4-carboxylic acid.

34. 7α-Methoxy-3-(1-methyl-1H-tetrazol-5-yl)thiomethyl-7β-[(4-N-methylcarbamoyl-3-hydroxyisoxazol-5-yl)acetamido]-3-cephem-4-carboxylic acid.

35. 7β-[(4-Cyano-3-hydroxyisoxazol-5-yl)acetamido]-7α-methoxy-3-(1-methyl-1H-tetrazol-5-yl)thiomethyl-3-cephem-4-carboxylic acid.

36. 7β-[(3-Benzenesulphonyloxy-4-carboxyisoxazol-5-yl)acetamido]-7α-methoxy-3-(1-methyl-1H-tetrazol-5-yl)thiomethyl-3-cephem-4-carboxylic acid.

37. 7β-[(4-N,N-Dimethylcarbamoyl-3-hydroxyisoxazol-5-yl)acetamido]-7α-methoxy-3-(1-methyl-1H-tetrazol-5-yl)thiomethyl-3-cephem-4-carboxylic acid.

38. 7β-[(4-Cyano-3-hydroxyisoxazol-5-yl)acetamido]-7α-methoxy-3-(5-methyl-1,3,4-thiadiazol-2-yl)thiomethyl-3-cephem-4-carboxylic acid.

39. 7β-[(3-Benzenesulphonyloxyisoxazol-5-yl)methylthioacetamido]-7α-methoxy-3-(1-methyl-1H-tetrazol-5-yl)thiomethyl-3-cephem-4-carboxylic acid.

40. 7β-[(3-Hydroxyisoxazol-5-yl)methylthioacetamido]-7α-methoxy-3-(1-methyl-1H-tetrazol-5-yl)thiomethyl-3-cephem-4-carboxylic acid.

41. 7β-[(3-Benzoyloxyisoxazol-5-yl)methylsulphonylacetamido]7α-methoxy-3-(1-methyl-1H-tetrazol-5-yl)thiomethyl-3-cephem-4-carboxylic acid.

42. 7β-[(3-Hydroxyisoxazol-5-yl)methylsulphonylacetamido]7α-methoxy-3-(1-methyl-1H-tetrazol-5-yl)thiomethyl-3-cephem-4-carboxylic acid.

43. 7β-[(4-Chloro-3-hydroxyisoxazol-5-yl)methylthioacetamido]7α-methoxy-3-(1-methyl-1H-tetrazol-5-yl)thiomethyl-3-cephem-4-carboxylic acid.

44. 7β-[(4-Chloro-3-hydroxyisoxazol-5-yl)methylsulphonylacetamido]7α-methoxy-3-(1-methyl-1H-tetrazol-5-yl)thiomethyl-3-cephem-4-carboxylic acid.

45. 7β-[(4-Bromo-3-mesyloxyisoxazol-5-yl)methylsulphonylacetamido]7α-methoxy-3-(1-methyl-1H-tetrazol-5-yl)thiomethyl-3-cephem-4-carboxylic acid.

46. 7β-[(4-Bromo-3-hydroxyisoxazol-5-yl)methylsulphonylacetamido]-7α-methoxy-3-(1-methyl-1H-tetrazol-5-yl)thiomethyl-3-cephem-4-carboxylic acid.

47. 7β-[(3-Hydroxy-4-methoxycarbonylisoxazol-5-yl)methylthioacetamido]-7α-methoxy-3-(1-methyl-1H-tetrazol-5-yl)thiomethyl-3-cephem-4-carboxylic acid.

48. 7β-[(3-Hydroxy-4-methoxycarbonylisoxazol-5-yl)methylsulphonylacetamido]-7α-methoxy-3-(1-methyl-1H-tetrazol-5-yl)thiomethyl-3-cephem-4-carboxylic acid.

49. 7β-[(4-Carboxy-3-hydroxyisoxazol-5-yl)methylthioacetamido]7α-methoxy-3-(1-methyl-1H-tetrazol-5-yl)thiomethyl-3-cephem-4-carboxylic acid.

50. 7β-[(4-Carboxy-3-hydroxyisoxazol-5-yl)methylsulphonylacetamido]-7α-methoxy-3-(1-methyl-1H-tetrazol-5-yl)thiomethyl-3-cephem-4-carboxylic acid.

51. 3-Acetoxymethyl-7β-[(3-hydroxyisoxazol-5-yl)methylthioacetamido]-7α-methoxy-3-cephem-4-carboxylic acid.

52. 7β-[(3-Hydroxyisoxazol-5-yl)methylthioacetamido]-7α-methoxy-3-(5-methyl-1,3,4-thiadiazol-2-yl)thiomethyl-3-cephem-4-carboxylic acid.

53. 3-Carbamoyloxymethyl-7β-[(3-hydroxyisoxazol-5-yl)methylthioacetamido]-7α-methoxy-3-cephem-4-carboxylic acid.

54. 7β-[(4-Carbamoyl-3-hydroxyisoxazol-5-yl)methylsulphonylacetamido]-7α-methoxy-3-(1-methyl-1H-tetrazol-5-yl)thiomethyl-3-cephem-4-carboxylic acid.

55. 7β-[(3-Hydroxy-4-N-methylcarbamoylisoxazol-5-yl)methyl-sulphonylacetamido]-7α-methoxy-3-(1-methyl-1H-tetrazol-5-yl)thiomethyl-3-cephem-4-carboxylic acid.

56. 7β-[(4-Cyano-3-hydroxyisoxazol-5-yl)methylthioacetamido]7α-methoxy-3-(1-methyl-1H-tetrazol-5-yl)thiomethyl-3-cephem-4-carboxylic acid.

57. 7β-[(4-Cyano-3-hydroxyisoxazol-5-yl)methylsulphonylacetamido]7α-methoxy-3-(1-methyl-1H-tetrazol-5-yl)thiomethyl-3-cephem-4-carboxylic acid.

58. 7β-[(4-N,N-Dimethylcarbamoyl-3-hydroxyisoxazol-5-yl)methylthioacetamido]-7α-methoxy-3-(1-methyl-1H-tetrazol-5-yl)thiomethyl-3-cephem-4-carboxylic acid.

59. 7β-[(4-Cyano-3-hydroxyisoxazol-5-yl)methylthioacetamido]-7α-methoxy-3-(5-methyl-1,3,4-thiadiazol-2-yl)thiomethyl-3-cephem-4-carboxylic acid.

60. 7β-[(4-Cyano-3-hydroxyisoxazol-5-yl)methylsulphonylacetamido]-7α-methoxy-3-(5-methyl-1,3,4-thiadiazol-2-yl)thiomethyl-3-cephem-4-carboxylic acid.

Of these compounds, particularly preferred Compounds are those numbered 1, 2, 6, 7, 10, 22, 24, 28, 41 and 42.

A number of methods are available for preparing the novel compounds of the present invention. Various methods which may be used for their preparation are as follows.

Method (I)

Compounds of formula (I) can be prepared by reacting a compound of formula (IV):

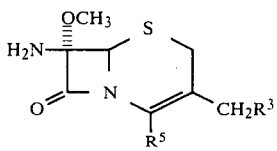

(in which R$^3$ is as defined above and R$^5$ represents a protected carboxyl group or a group of formula COOM, where M represents a salt-forming cation) with an acid halide of general formula (V):

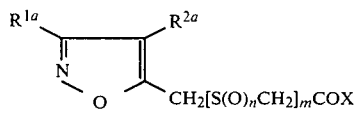

(in which: R$^{1a}$ represents any of the groups defined for R$^1$ or a protected hydroxy group; R$^{2a}$ represents any of the groups defined for R$^2$ or a protected carboxyl group; X represents a halogen atom and m and n are as defined above) to give a compound of formula (X):

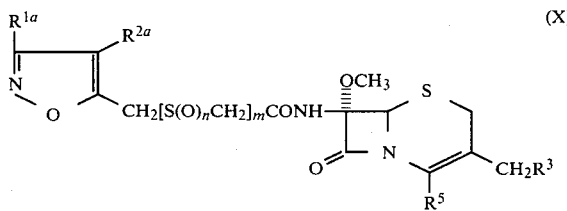

and, if necessary, removing the carboxy-protecting group or groups and, if necessary removing the hydroxy-protecting group.

The compounds of formula (IV) used as starting materials in this Method may be prepared, for example, by the methods disclosed in Japanese Patent Publications (unexamined) No. 50394/75 and 117793/75. The compounds of general formula (V) which are the other starting materials for use in this Method may be prepared, for example where m=0, by the methods described in Japanese Patent Publications (unexamined) No. 29591/75 or No. 42360/78, the Journal of the Chemical Society, 1968, pages 172–184 or the Journal of the American Chemical Society, 100, pages 3609–3611 (1978). Compounds of formula (V) where m=1 are novel compounds and may be obtained from the appropriate substituted isoxazole (3—R$^{1a}$—4-R$^{2a}$-5-methylisoxazole)[the Journal of the Chemical Society, page 172 (1968)] e.g. by: Bromination with N-bromosuccinimide; reaction with thioglycolic acid and with diphenyldiazomethane; protection of the 3-hydroxy group; and reaction with trifluoroacetic acid and with phosphorus pentachloride.

There is no particular limitation upon the nature of the carboxy-protecting group used to form group R$^5$ in the compound of formula (IV) and any such group conventionally used in this art may be employed. Examples of protecting groups to form group R$^5$ include: the benzhydryl group, the p-methoxybenzyl group, the t-butyl group, the benzyloxymethyl group, the methoxymethyl group, the p-bromo-phenacyl group and the trimethylsilyl group. Where the group R$^5$ represents a group of formula COOM, the cation M may be an alkali metal atom, e.g. sodium, potassium or lithium, an ammonium group or a group derived from an organic base, such as diisopropylamine or pyridine.

Where the group R$^1$ in the final product of formula (I) represents a hydroxy group, the corresponding group R$^{1a}$ in the compound of formula (V) may represent a hydroxy group, but is preferably a protected hydroxy group, for example an aliphatic, aromatic or araliphatic acyloxy group or an aliphatic, aromatic or araliphatic sulphonyloxy group, more preferably an aromatic acyloxy group or an aliphatic, aromatic or araliphatic sulphonyloxy group. Where the group R$^{2a}$ in the compound of formula (V) represents a protected carboxyl group, this is preferably an alkoxycarbonyl group, a benzhydryloxycarbonyl group, a p-methoxybenzyloxycarbonyl group, a t-butoxycarbonyl group, a benzyloxymethoxycarbonyl group, a methoxymethoxycarbonyl group, a p-bromophenacyloxycarbonyl group or a trimethylsilyloxycarbonyl group; any of these groups can be converted into a free carboxyl group by removing the protecting group from the compound of formula (X) as hereafter described.

The preparation of the compound of formula (X) may be carried out by reacting the compound of formula (IV) with the acid halide of formula (V) in the presence of an acid binding agent and in a suitable inert solvent. There is no particular limitation upon the nature of the solvent, provided that it has no adverse effect upon the reaction. Preferred solvents are halogenated hydrocarbons, such as methylene chloride, dichloroethane or chloroform. Examples of suitable acid binding agents are: dialkylanilines (e.g. dimethylaniline or diethylaniline); heterocyclic bases (e.g. pyridine or picoline); trialkylamines (e.g. triethylamine or tributylamine); alkali metal hydrogen carbonates (e.g. sodium hydrogen carbonate or potassium hydrogen carbonate); and propylene oxide.

The preferred acid halide of formula (V) is the acid chloride, i.e. X represents a chlorine atom.

There is no particular limitation upon the reaction temperature and, for this reason, we prefer to carry out the reaction at a temperature between 0° C. and room temperature. The time required for the reaction will vary depending upon the reaction temperature, the reagents and other factors, but will normally be from 15 minutes to 2 hours.

After completion of the reaction, the compound of formula (X) may be recovered from the reaction mixture by conventional means. For example, the reaction mixture may be washed with water and then the solvent distilled off. If necessary, the resulting residue may be further purified by conventional means such as column chromatography or preparative thin layer chromatography.

The compound of formula (X) thus prepared may, if necessary, be converted to the desired compound of formula (I) by removal of any protecting groups or, where R$^5$ represents a group of formula COOM, by conversion of the salt to the corresponding acid.

The nature of the reaction employed to remove the carboxyl-protecting group or groups will depend upon the nature of the group and methods for removing such groups are well-known in the art. For example, where the carboxyl group has been protected by conversion to a methoxymethyl ester or t-butyl ester, it may be restored by contacting the compound of formula (X) with a dilute acid in a suitable inert solvent. Where the carboxyl group has been protected by conversion to a benzyl ester, the carboxyl group may be restored by reducing the ester in the presence of a palladium catalyst and in a suitable inert solvent. Where, as is most preferred, the carboxyl group has been protected by conversion to a benzhydryl (diphenylmethyl) ester, the carboxyl group can be restored by contacting the compound of formula (X) with trifluoroacetic acid in a suitable inert organic solvent.

Where $R^{1a}$ in the compound of formula (X) represents an aliphatic, aromatic or araliphatic acyloxy group or an aromatic, aliphatic or araliphatic sulphonyloxy group, it may be converted to a hydroxy group by treating the compound of formula (X) with a base in the presence of an aqueous solvent. There is no particular limitation upon the nature of the aqueous solvent employed for this reaction and, indeed, any such solvent commonly used in hydrolysis may be employed. Preferred solvents are water or a mixture of water with an organic solvent, such as an alcohol (e.g. methanol, ethanol or n-propanol), a ketone (e.g. acetone or methyl ethyl ketone) or an ether (e.g. tetrahydrofuran or dioxan). There is also no particular limitation upon the nature of the base employed, provided that it does not affect other parts of the compound, particularly the β-lactam ring. Examples of suitable bases are: aqueous ammonia; alkali metal phosphates, e.g. disodium hydrogen phosphate or dipotassium hydrogen phosphate; and alkali metal hydrogen carbonates, e.g. sodium hydrogen carbonate or potassium hydrogen carbonate. The reaction is preferably carried out at a pH value from 7 to 10. There is no particular limitation upon the reaction temperature and, accordingly, in order to avoid or reduce side reactions, we prefer to carry out the reaction at a temperature from 0° C. to about room temperature. The time required for the reaction will vary, depending upon the nature of the acyloxy or sulphonyloxy group in the starting material, the reaction temperature and other reaction conditions. However, in general, the reaction will be substantially complete within from 1 to 6 hours.

Where this Method has been used to prepare a compound of formula (I) in which $R^1$ represents an aliphatic acyloxy group, a substituted or unsubstituted benzoyloxy group, a substituted or unsubstituted benzenesulphonyloxy group or a substituted or unsubstituted alkanesulphonyloxy group, these groups may, of course, be converted to hydroxy group by the process just described.

After completion of the reaction, the desired product of formula (I) can be recovered from the reaction mixture by conventional means. Where a base has been used in the reaction, a suitable sequence of recovery steps comprises: adjusting the pH of the reaction mixture to about 2; extracting the mixture with an organic solvent; distilling off the organic solvent under reduced pressure; and adding to the residue an organic solvent (such as diisopropyl ether) which is capable of precipitating the desired compound. The product thus obtained may, if desired, be further purified by conventional means, for example reprecipitation or preparative thin layer chromatography.

Method (II)

A compound of formula (VI):

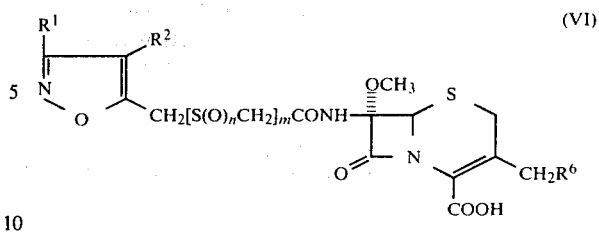

[in which $R^1$, $R^2$, m and n are as defined above and $R^6$ represents a tetrazolylthio, thiadiazolylthio or oxadiazolythio group optionally substituted with a $C_1$–$C_3$ alkyl, sulphomethyl or di($C_1$ or $C_2$ alkyl)-amino($C_1$–$C_3$ alkyl) substituent] may be prepared by reacting a compound of formula (VII):

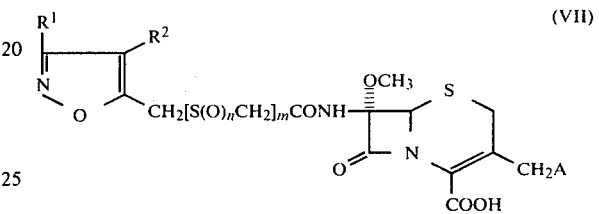

(in which $R^1$, $R^2$, m and n are as defined above and A represents an acetoxy group or a carbamoyloxy group) or a salt or ester thereof with a heterocyclic thiol of formula (XI):

(in which $R^6$ is as defined above) or an alkali metal salt thereof.

The compound of formula (VII), which is one of the starting materials for use in this Method, falls within the definition of the compound of formula (I) and may be prepared by Method (I), described above. Suitable salts of compound (VII) are the alkali metal (e.g. sodium or potassium) salts or the ammonium salts. Suitable esters are those referred in Method (I) in connection with the protected carboxyl group $R^5$, although the use of esters is not preferred due to possible double bond migration in the cephem ring.

The process can be carried out by reacting the compound of formula (VII) or a salt or ester thereof with the heterocyclic thiol of formula (XI) or an alkali metal salt thereof (e.g. the sodium salt or potassium salt). Examples of heterocyclic thiols of formula (XI) are tetrazole-5-thiol, thiadiazoe-2-thiol and oxadiazole-2-thiol, the heterocyclic ring of which may be unsubstituted or may have one or more alkyl, sulphomethyl or dialkylaminoalkyl substituents, as in the above definition of $R^6$. The reaction is preferably carried out in the presence of a solvent, the nature of which is not critical, provided that it does not adversely affect the reaction. We prefer to use water or an organic solvent such as ethanol or acetone. Where the organic solvent is water-miscible, it may be used together with water. The reaction is desirably carried out under weakly acidic or weakly alkaline conditions. Accordingly, where the free carboxylic acid of formula (VII) is used, we prefer to carry out the reaction in the presence of an alkaline hydroxide or alkaline phosphate in an aqueous solution. Under these alkaline conditions, where $R^1$ in the compound of formula (VII) represents an acyloxy group, it will normally be converted to a hydroxy group. There is no particular limitation upon the reaction temperature, and we therefore prefer to employ either a temperature about room temperature or a temperature from 60° to 100° C.

After completion of the reaction, the compound of formula (VI) thus obtained can be recovered from the reaction mixture by conventional means, for example acidifying the reaction mixture and collecting the product precipitated by filtration. Alternatively, after extracting the reaction mixture with an organic solvent, the extract can be dried and the solvent distilled off. If desired, the resulting product can be further purified by, for example, preparative thin layer chromatography.

Method (III)

A compound of formula (I) in which $R^3$ represents a carbamoyloxy group, that is to say a compound of formula (VIII):

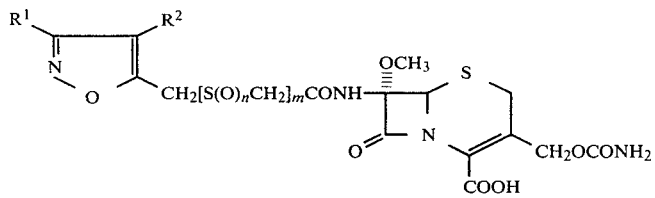

(in which $R^1$, $R^2$, m and n are as defined above) can also be prepared by protecting the amino group and the carboxyl groups of cephamycin C, which has the formula (IX):

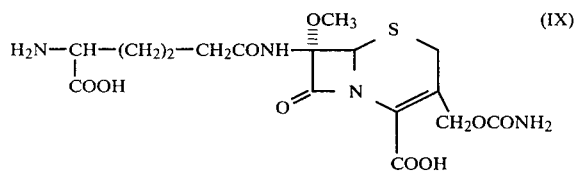

reacting the resulting compound with an acid halide of formula (V), defined in Method (I), in the presence of a molecular sieve or a silylating agent and then removing the carboxyl-protecting group or groups and, if necessary, the hydroxy-protecting group.

This method thus comprises the following steps:

(i) protecting the amino group in the side chain at the 7β-position of the cephamycin C;

(ii) protecting the carboxyl groups;

(iii) acylating with the acid halide of formula (V); and (iv) restoring the carboxyl group or groups and, if necessary, the hydroxy group.

In step (i) the amino group in the side chain of the cephamycin C [which is removed in step (iii)] is protected, in order to prevent side reactions which might be caused by this amino group. There is no particular limitation upon the nature of the protecting group employed and any group capable of being introduced onto an amino group and not interferring with subsequent reaction may be used. For example, reaction of the cephamycin C with an acyl halide or acyl anhydride (e.g. acetyl chloride, benzoyl chloride or acetic anhydride) will protect the amino group by introduction of an acyl group. An alkoxycarbonyl group may be introduced by reaction of the cephamycin C with a reactive derivative of an alkyl or aralkyl carbonate, e.g. methyl chlorocarbonate, ethyl chlorocarbonate, isobutyl chlorocarbonate, benzyloxycarbonyl chloride or t-butoxycarbonyl azide. Alternatively, the amino group may be protected by introduction of an arylsulphonyl group by reaction of the cephamycin C with an arylsulphonyl halide, e.g. benzenesulphonyl chloride or p-toluenesulphonyl chloride. There is no particular limitation upon the reaction conditions employed for the introduction of these protecting groups and conditions well-known in the art for this type of reaction may be used. In general, the reaction is carried out by contacting the cephamycin C with the agent introducing the protecting group in the presence or absence of a base and in the presence of a suitable solvent. The time required for the reaction is normally several hours. After completion of the reaction, the desired compound may be recovered from the reaction mixture by conventional means. For example, if water has been used as the reaction solvent, the reaction mixture is acidified and extracted with a suitable organic solvent; the solvent is then distilled off. Where an organic solvent is used as the reaction solvent, the solvent is distilled off or water is added to the mixture without distillaion of the solvent and, after acidification the mixture is treated as in the case where water was used as the reaction solvent. The compound thus obtained can, if desired, be purified by conventional means.

In step (ii), the free carboxyl groups in the cephamycin C are blocked in order to prevent their reaction with the acid halide in step (iii) and the resulting reduced yields. When the step (iii) reaction with the acid halide is carried out in the presence of a silylating agent, the carboxyl group is protected by the silylating agent and, accordingly, step (ii) is carried out simultaneously with step (iii). In this case, the silyl group is removed in subsequent treatment in the course of step (iii) and thus the desired compound is obtained as the free acid without the optional fourth step. Where a carboxyl-protecting group other than the silyl group is employed, it may be any protecting group which can later be removed under mild conditions without affecting other parts of the cephem nucleus. Examples of such groups include the benzhydryl group, the t-butyl group, the methoxymethyl group and substituted or unsubstituted benzyl groups. Reaction to introduce these protecting groups may be carried out under conventional conditions.

Step (iii) is a transacylation step in which the monoacylamido side chain at the 7β-position is converted to a diacylamido group and then, almost simultaneously, the original acyl group is removed. This reaction may be carried out by contacting the compound obtained in step (ii) with an acid halide of general formula (V) in the presence of a molecular sieve or of a silylating agent, normally in the presence of a suitable solvent. Where the reaction is carried out in the presence of a silylating agent, the compound obtained in step (i) is used and step (ii) may be omitted, as described above, since the compound is converted to a silyl ester in the reaction system. In this case, the silylating agent is preferably used in excess. The solvent is preferably an aprotic solvent, for example a halogenated hydrocarbon, a cyclic ether or an acetic acid ester. Instead of carrying out the reaction in the presence of a silylating agent, it may be carried out in the presence of a molecular sieve, preferably Molecular Sieve 3A, 4A or 5A (a product of Nippon Chromato Kogyo Company). There is no particular limitation upon the nature of the silylating agent and any such agent commonly used for the silylation of an active hydrogen atom may be employed. Preferred silylating agents are N-silylamide compounds, such as N-(trimethylsilyl)acetamide, N,N-bis(-trimethylsilyl)acetamide, N-(trimethylsilyl)trichloroacetamide, N-(trimethylsilyl)trifluoroacetamide, N,N-bis(trimethylsilyl)trichloroacetamide or N,N-bis(-trimethylsilyl)trifluoroacetamide. There is no particular limitation upon the reaction temperature, but we prefer to employ room temperature or a slightly elevated temperature, temperatures from 50° to 70° C. being most preferred. The time required for the reaction will vary, depending upon the reagents and the reaction temperature and other conditions, a period from several hours to 20 or 30 hours being common. After completion of the reaction, the desired compound may be recovered by conventional means. A suitable recovery sequence comprises:

filtering off insolubles;
optionally washing the filtrate with water; and
distilling off the solvent.

If the reaction mixture is a uniform phase, the filtration step may be omitted and the reaction mixture simply washed, if desired, with water and then the solvent distilled off. The residue may, if necessary, be further purified by, for example, column chromatography. Where the silyl ester is produced in the course of this step, it is decomposed during subsequent treatment to give a compound having a free carboxyl group and thus step (iv) may not be required.

In step (iv), the protected carboxyl group or groups and/or the protected hydroxy group are restored. The carboxyprotecting group may be removed by conventional means, which may vary depending upon the nature of the group, as described in Method (I). Similarly, where a hydroxy-protecting group is to be removed, this may also be done as described in Method (I). After completion of the reaction, the desired product may be recovered from the reaction mixture by a conventional sequence of steps. A suitable sequence comprises, for example:

filtering off insolubles, if any, from the reaction mixture;
optionally distilling off the solvent and/or excess reagents;
dissolving the reaction mixture or the filtrate or the residue obtained by distillation from the filtrate in a suitable solvent;
washing the solution with water; and
distilling off the solvent.

The residue may, if necessary, be further purified by re-extraction or by column chromatography or by conversion to a suitable crystalline salt, generally an amine salt.

The compound of formula (I) thus obtained may be converted to a pharmaceutically acceptable non-toxic salt, (e.g. an alkali metal salt, an ammonium salt or a salt with an organic base) by conventional means. Similarly, if desired, the acid may be converted into an ester by conventional means.

The compounds of the invention are potent antibacterial agents and, as already explained, against certain bacteria have activities equivalent to or even greater than the corresponding compounds having a hydrogen atom at the $7\alpha$-position. The activity of certain of the compounds of the invention is illustrated by the following Tables 1 and 2, which give results for the minimal inhibitory concentrations (MIC in $\gamma$/ml) of various of the compounds of the invention. In Table 1, the MIC values of certain compounds of the invention are contrasted with the values of corresponding compounds having a hydrogen atom at the $7\alpha$-position. In the Tables, the compounds of the invention are identified by the numbers heretofore assigned to them. The prior art compounds having a hydrogen atom at the $7\alpha$-position are identified by the number of their corresponding compound with a methoxy group at the $7\alpha$-position together with the suffix A. Activity was tested by the Agar plate dilution method. The microorganisms against which the compounds were tested are identified in the Tables as follows:

I: *Staphylococcus aureus* 209P
II: *Staphylococcus aureus* 56
III: *Escherichia coli* NIHJ
IV: *Escherichia coli* 609
V: *Shigella flexneri* 2a
VI: *Klebsiella pneumoniae* 806
VII: *Proteus vulgaris*
VIII: *Proteus rettgeri*
IX: *Salmonella enteritidis* G.

TABLE 1

| Microorganism No. | Compound No. | | | |
|---|---|---|---|---|
| | 2 | 2A | 28 | 28A |
| I | 3.1 | 0.8 | 3.1 | 3.1 |
| II | 6.2 | 1.5 | 3.1 | 6.2 |
| III | 0.8 | 3.1 | 0.4 | 12.5 |
| IV | 0.8 | 50 | 0.4 | 100 |
| V | 1.5 | 3.1 | 0.4 | 6.2 |
| VI | 0.8 | 0.8 | 0.4 | 3.1 |
| VII | 1.5 | 12.5 | 1.5 | 12.5 |
| VIII | 0.4 | 0.4 | 0.4 | 12.5 |
| IX | 0.4 | 0.8 | 0.2 | 3.1 |

TABLE 2

| Cpd No. | Microorganism No. | | | | | | | | |
|---|---|---|---|---|---|---|---|---|---|
| | I | II | III | IV | V | VI | VII | VIII | IX |
| 1 | 3.1 | 6.2 | 0.8 | 0.8 | 1.5 | 0.8 | 1.5 | 0.4 | 0.4 |
| 2 | 3.1 | 12.5 | 0.8 | 0.8 | 0.8 | 0.8 | 3.1 | 0.4 | 0.4 |
| 3 | 0.8 | 1.5 | 3.1 | 3.1 | 3.1 | 3.1 | 3.1 | 1.5 | 0.8 |
| 4 | 3.1 | 6.2 | 3.1 | 3.1 | 6.2 | 3.1 | 12.5 | 1.5 | 1.5 |
| 6 | 1.5 | 3.1 | 0.4 | 0.2 | 0.4 | 0.2 | 0.4 | $\leq$0.1 | $\leq$0.1 |
| 7 | 3.1 | 6.2 | 0.4 | 0.4 | 0.4 | 0.2 | 0.8 | $\leq$0.1 | $\leq$0.1 |
| 10 | 0.8 | 6.2 | 0.4 | 0.4 | 0.8 | 0.4 | 1.5 | 0.4 | 0.4 |
| 21 | 0.4 | 0.8 | 3.1 | 3.1 | 6.2 | 3.1 | 6.2 | 1.5 | 1.5 |

TABLE 2-continued

| Cpd No. | Microorganism No. | | | | | | | | |
|---|---|---|---|---|---|---|---|---|---|
| | I | II | III | IV | V | VI | VII | VIII | IX |
| 22 | 1.5 | 3.1 | 0.4 | 0.4 | 0.2 | ≦0.1 | 0.4 | ≦0.1 | ≦0.1 |
| 24 | 0.8 | 3.1 | 0.2 | 0.2 | 0.2 | ≦0.1 | 0.8 | ≦0.1 | ≦0.1 |
| 27 | 6.2 | 6.2 | 0.8 | 0.8 | 0.8 | 0.8 | 3.1 | 0.8 | 0.4 |
| 28 | 3.1 | 3.1 | 0.4 | 0.4 | 0.4 | 0.4 | 1.5 | 0.4 | 0.2 |
| 39 | 0.2 | 0.4 | 1.5 | 3.1 | 1.5 | 0.8 | 0.8 | 0.2 | 0.4 |
| 40 | 1.5 | 3.1 | 0.8 | 0.8 | 0.8 | 0.2 | 0.2 | ≦0.1 | ≦0.1 |
| 41 | 3.1 | 6.2 | 0.8 | 0.8 | 0.8 | 0.4 | 0.4 | 0.1 | 0.1 |
| 42 | 6.3 | 6.2 | 0.4 | 0.4 | 0.8 | 0.2 | 0.4 | 0.1 | 0.1 |
| 43 | 1.5 | 1.5 | 1.5 | 3.1 | 0.8 | 0.8 | 0.4 | ≦0.01 | 0.1 |
| 44 | 6.2 | 6.2 | 0.8 | 1.5 | 0.8 | 0.4 | 0.8 | 0.1 | 0.1 |

As can be seen from the results given in the above Tables, the compounds of the invention have excellent antibacterial activity against a wide range of pathogenic microorganisms and are, therefore, useful as antibacterial agents. The compounds can be administered orally or parenterally, for example in the form of capsules, tablets or injections; they are preferably administered parenterally by injection.

The dosage depends upon the age, symptoms, body weight of the patient and the course and duration of treatment, but a common dosage may range from 250 mg to 3,000 mg per day for an adult; however, if necessary, larger dosages may be employed.

The invention thus also provides a pharmaceutical composition comprising the novel 7α-methoxycephalosporin derivatives of formula (I) or a salt or ester thereof in admixture with a pharmaceutically acceptable carrier or diluent. Any conventional pharmaceutical carrier or diluent may be employed, the nature of the carrier or diluent depending upon the intended route of administration. Where the composition is intended to be administered orally, it is desirably presented in a form readily absorbed from the stomach or intestines. Tablets or capsules for oral administration are normally in unit dosage form and may contain binding agents (e.g. syrup, gum arabic, gelatine, sorbitol, gum tragacanth or polyvinylpyrrolidone), diluents (e.g. lactose, sugar, corn starch, calcium phosphate, sorbitol or glycine), lubricants (e.g. magnesium stearate, talc, polyethylene glycol or silica), disintegrating agents (e.g. potato starch) or wetting agents (e.g. sodium lauryl sulphate) or any combination thereof. The tablets may, if desired, be coated, e.g. with an enteric coating, as is well-known in the art.

Liquid formulations for oral administration may be aqueous or oily suspensions, solutions, syrups, elixirs or similar compositions. Alternatively, the composition may be a dried product which can then be redissolved in water or another suitable vehicle before administration. Such solutions may contain conventional additives, such as suspending agents, (e.g. sorbitol syrup, methycellulose, glucose/sugar syrup, gelatine, hydroxyethylcellulose, carboxymethylcellulose, aluminum stearate gel or hydrogenated edible fat), emulsifying agents (e.g. lecithin, monooleic acid sorbitol or gum arabic), non-aqueous vehicles (e.g. almond oil, fractionated coconut oil, oily esters, propylene glycol or ethyl alcohol), or antiseptics (e.g. methyl p-hydroxybenzoate, propyl p-hydroxybenzoate or sorbic acid) or any combination of two or more thereof.

Compositions for injection are preferably provided in a unit dosage ampoule or a multiple dosage vessel together with antiseptics. A composition formulated for injection may be in the form of a suspension, solution or emulsion, in an aqueous or oily vehicle and may contain emulsifying agents, stabilizers or dispersing agents (such as those exemplified above) or any combination of two or more thereof. Alternatively, the active ingredient may be provided as a powder which is redissolved, prior to administration, in a suitable vehicle, such as sterile, pyrogen-free water.

When the composition of the invention is formulated as a unit dose, it preferably contains from 250 to 500 mg of the compound of the invention per unit dose.

The invention is further illustrated by the following Examples and Preparations. Examples 1 to 23 illustrate the preparation of compounds according to the present invention; Examples 24 to 26 illustrate pharmaceutical compositions containing the compounds of the invention; and the Preparations illustrate the preparation of various of the starting materials used in the Examples.

PREPARATION 1

Benzhydryl 3-hydroxyisoxazol-5-ylacetate

To an ice-cooled solution of 5.72 g (40 mmoles) of 3-hydroxyisoxazol-5-ylacetic acid in 50 ml of acetone was added dropwise a solution of 7.76 g (40 mmoles) of diphenyldiazomethane in 50 ml of acetone. The mixture was stirred for 1 hour in an ice bath. After confirming that the red colour of the diphenyldiazomethane had disappeared, the solvent was distilled off under reduced pressure and 100 ml of diisopropyl ether were added to the residue to precipitate crystals of the title compound, melting point 105°–106° C. The yield was 9.3 g (75% of theory).

Infrared absorption spectrum (Nujol-Trade Mark) $\nu cm^{-1}$:1750 (c=0).

Nuclear magnetic resonance spectrum (deuterated chloroform) δppm: 11.08 (singlet, 1H, OH); 7.42 [singlet, 10H, C(C$_6$H$_5$)$_2$]; 7.03 (singlet, 1H, OCH=); 6.00 (singlet, 1H, hydrogen at 4-position of isoxazole); 3.87 (singlet, 2H, CH$_2$).

PREPARATION 2

Benzhydryl 3-benzoyloxyisoxazol-5-ylacetate

A solution of 9.3 g (30 mmoles) of benzhydryl 3-hydroxyisoxazol-5-ylacetate, obtained as described in Preparation 1, in a mixture of 100 ml of methylene chloride and 100 ml of diethyl ether was cooled by ice. 3.0 g (30 mmoles) of triethylamine and 4.2 g (30 mmoles) of benzoyl chloride were then added, in turn, to the solution and the mixture was stirred for 2 hours. At the end of this time, 200 ml of diethyl ether were added and the reaction mixture was washed, in turn, with 100 ml of water and with 100 ml of an aqueous solution of sodium chloride. The solution was then dried over anhydrous sodium sulphate and then the solvent was distilled off under reduced pressure. After washing the residue with diethyl ether, 10 g (yield 80% of theory) of the title compound, melting point 95°–96° C., were obtained.

Infrared absorption spectrum (Nujol) $v cm^{-1}$: 1760, 1750 (C=O).

Nuclear magnetic resonance spectrum (deuterated chloroform) δppm: 7.30–8.50 (multiplet, 5H, $C_6H_5CO$); 7.40 [singlet, 10H, $C(C_6H_5)_2$]; 7.00 (singlet, 1H, OCH=); 6.62 (singlet, 1H, hydrogen at 4-position of isoxazole); 3.95 (singlet, 2H, $CH_2$).

PREPARATION 3

3-Benzoyloxyisoxazol-5-ylacetic acid 8.3 g (20 mmoles) of benzhydryl 3-benzoyloxyisoxazol-5-ylacetate, obtained as described in Preparation 2, were dissolved in 30 ml of methylene chloride, and then 8 ml of anisole were added thereto. After ice-cooling the mixture, 27 ml of trifluoroacetic acid were added and the mixture was stirred for 3 hours. At the end of this time, the solvent was distilled off under reduced pressure and the residue was recrystallized from diethyl ether. The title compound was obtained in a yield of 3.7 g (75% of theory). This product was recrystallized from a mixture of ethyl acetate and ethanol to give crystals melting at 133°–134° C.

Nuclear magnetic resonance spectrum (deuterated dimethyl sulphoxide) δppm: 7.40–8.40 (multiplet, 5H, $C_6H_5$); 6.60 (singlet, 1H, hydrogen at 4-position of isoxazole); 3.73 (singlet, 1H, $CH_2$).

PREPARATION 4

3-mesyloxyisoxazol-5-ylacetic acid

To a solution of 3.1 g (10 mmoles) of 3-hydroxyisoxazol-5-ylacetic acid in 50 ml of ethyl acetate were added successively 1.0 g of triethylamine and 1.15 g of methanesulphonyl chloride at room temperature; the mixture was then stirred for 1 hour. At the end of this time, the solution was washed with, in turn, water, aqueous sodium hydrogen carbonate and aqueous sodium chloride; the solution was then dried over anhydrous sodium sulphate. The solvent was distilled off from the dried solution and diisopropyl ether was added to the residue to give 3.3 g (85%) of crystals of benzhydryl 3-mesyloxyisoxazol-5-ylacetate, melting point 102°–103° C.

Nuclear magnetic resonance spectrum (deuterated chloroform) δppm: 7.30 [singlet, 10H, $C(C_6H_5)_2$]; 6.90 (singlet, 1H, OCH=); 6.25 (singlet, 1H, hydrogen at 4-position of isoxazole); 3.90 (singlet, 2H, $CH_2$); 3.30 (singlet, 3H, $CH_3$).

To a solution of 3.9 g of the benzhydryl ester prepared as described above in 20 ml of methylene cloride were added 5 ml of anisole; 20 ml of trifluoroacetic acid were then added dropwise to this solution under ice-cooling. The mixture was stirred under ice-cooling for 1 hour and then at room temperaure for 1 hour. The solvent was then distilled off under reduced pressure, and the residue was dissolved in diisopropyl ether and reprecipitated by the addition of hexane, to give 2.0 g (90%) of the title compound, melting point 101°–103° C.

Elemental analysis
Calculated for $C_6H_7NO_6S$: C, 32.58%; H, 3.19%; N, 6.33%; S, 14.45%. Found C, 32.48%; H, 3.21%; N, 6.30%; S, 14.48%.

PREPARATION 5

3-Ethanesulphonyloxyisoxazol-5-ylacetic acid

To a solution of 1.55 g (5 mmoles) of benzhydryl 3-hydroxyisoxazol-5-ylacetate in 20 ml of ethyl acetate were added 0.71 ml (5.1 mmoles) of triethylamine and 0.48 ml (5.05 mmoles) of ethanesulphonyl chloride at room temperature. The mixture was stirred for 1 hour and then washed with, in turn, water, aqueous sodium hydrogen carbonate and aqueous sodium chloride; the solution was then dried over anhydrous magnesium sulphate. The solvent was then distilled off and the residue was purified by column chromatography eluted with a 20:1 by volume mixture of benzene and ethyl acetate to give 1.56 g of the benzhydryl ester of the title compound.

1.5 g of this ester were dissolved in a mixture of 10 ml of methylene chloride and 1 ml of anisole; 5 ml of trifluoroacetic acid were then added, with ice-cooling. The solution was stirred at room temperature for 0.5 hour. At the end of this time, the solvent was distilled off and ethyl acetate was added to the residue. The solution was then extracted with a 10% w/v aqueous solution of potassium dihydrogen phosphate. The pH of the extract was adjusted to a value of 2.0 by adding 3 N hydrochloric acid and then the solution was extracted with ethyl acetate to give 0.69 g of the title compound.

PREPARATION 6

3-Benzenesulphonyloxyisoxazol-5-ylacetic acid

To a solution of 1.55 g (5 mmoles) of benzhydryl 3-hydroxyisoxazol-5-ylacetate in 20 ml of ethyl acetate were added 0.71 ml (5.1 mmoles) of triethylamine and 0.65 ml (5.05 mmoles) of benzenesulphonyl chloride. After stirring the mixture for 1 hour, it was washed with water and then dried. The solvent was distilled off to give the benzhydryl ester of the title compound quantitatively. The ester was then treated in the same manner as described in Preparation 5, affording 1.30 g of the title compound.

PREPARATION 7

4-Chloro-3-hydroxyisoxazol-5-ylacetic acid

To a solution of 4.3 g (30 mmoles) of 3-hydroxyisoxazol-5-ylacetic acid in 10 ml of N,N-dimethylformamide were added 4.81 g (36 mmole) of N-chlorosuccinimide, with ice-cooling and stirring. The mixture was left to stand at room temperature for 15 hours, after which the N,N-dimethylformamide was distilled off under reduced pressure and ethyl acetate was added. The mixture was then extracted with an aqueous solution of sodium hydrogen carbonate and then the pH of the extract was adjusted to a value below 1.0 by addition of concentrated hydrochloric acid. After drying the solution, the solvent was distilled off and the residue was recrystallized from a 1:5 by volume mixture of ethyl acetate and cyclohexane, to give 3.2 g (60%) of the title compound, melting point 155° C.

Elemental analysis:
Calculated for $C_5H_4NO_4Cl$: C, 33.82%; H, 2.27%; N, 7.89%; Cl, 19.97%. Found: C, 34.45%; H, 2.50%; N, 7.63%; Cl, 18.23%.

PREPARATION 8

4-Bromo-3-hydroxyisoxazol-5-ylacetic acid

To a solution of 6.0 g (35 mmoles) of 3-hydroxyisoxazol-5-ylacetic acid in 10 ml of N,N-dimethylformamide were added 6.5 g (42 mmoles) of N-bromosuccinimide, with ice-cooling and stirring. The mixture was stirred under ice-cooling for 2 hours and then at room temperature for 1 hour. The N,N-dimethylformamide was then distilled off under reduced pressure. The residue was dissolved in ethyl acetate and extracted with an aqueous solution of sodium hydrogen carbonate. The pH of the extract was adjusted to a value below 1.0 by the addition of concentrated hydrochloric acid, and then the solution was extracted with ethyl acetate. After drying the ethyl acetate extract, the solvent was distilled off. The crystals which formed the residue were recrystallized from a 1:5 by volume mixture of ethyl acetate and cyclohexane, giving 4.5 g (58%) of the title compound in the form of colourless plate crystals, melting point 167° C. with decomposition.

Elemental analysis:
Calculated for $C_5H_4NO_4Br$: C, 27.05%; H, 1.82%; N, 6.31%; Br, 36.00%. Found: C, 27.32%; H, 1.85%; N, 6.16%; Br, 35.75%.

PREPARATION 9

(3-Mesyloxy-4-methoxycarbonylisoxazol-5-yl)acetic acid

Diphenyldiazomethane was reacted with (3-hydroxy-4-methoxycarbonylisoxazol-5-yl)acetic acid [prepared by the method disclosed in the Journal of the American Chemical Society, 100, pages 3609–3611 (1978)] to give the benzhydryl ester of the acid. This benzhydryl ester was then reacted with methanesulphonyl chloride in the presence of triethylamine to afford benzhydryl (3-mesyloxy-4-methoxycarbonylisoxazol-5-yl)acetate.

Infrared absorption spectrum (liquid film) $\nu cm^{-1}$: 1735 (ester C=O).

Nuclear magnetic resonance spectrum (deuterated chloroform) δppm: 7.36 [singlet, 10H, C(C$_6$H$_5$)$_2$]; 6.97 (singlet, 1H, OCH=); 4.22 (singlet, 2H, CH$_2$); 3.70 (singlet, 3H, OCH$_3$); 3.41 (singlet, 3H, CH$_3$SO$_2$).

This ester was then treated with trifluoroacetic acid to give the title compound.

PREPARATION 10

3-Benzenesulphonyloxyisoxazol-5-ylmethylthioacetic acid

3-Hydroxy-5-methylisoxazole was reacted with benzoyl chloride in the presence of triethylamine to give 3-benzoyloxy-5-methylisoxazole, which was then reacted with N-bromosuccinimide, to give 3-benzoyloxy-5-bromomethylisoxazole. This was reacted with disodium thioglycolate to give 3-hydroxyisoxazol-5-ylmethylthioacetic acid, which was treated with diphenyldiazomethane to give the benzhydryl ester.

This benzhydryl 3-hydroxyisoxazol-5-ylmethylthioacetate was reacted with benzenesulphonyl chloride in the presence of triethylamine to give benzhydryl 3-benzenesulphonyloxyisoxazol-5-ylmethylthioacetate, which was treated with trifluoroacetic acid to afford the title compound as crystals.

Nuclear magnetic resonance spectrum (deuterated acetone) δppm: 7.02–8.15 (multiplet, 5H, C$_6$H$_5$); 6.43 (singlet, 1H, hydrogen at 4- position of isoxazole); 4.01 (singlet, 2H, —CH$_2$SCH$_2$CO—); 3.30 (singlet, 2H, —CH$_2$SCH$_2$CO—).

PREPARATION 11

3-Benzoyloxyisoxazol-5-ylmethylsulphonylacetic acid

3-Hydroxyisoxazol-5-ylmethylthioacetic acid (prepared as described in the first part of Preparation 10) was refluxed in ethanol in the presence of sulphuric acid to give the ethyl ester, which was then oxidized with m-chloroperbenzoic acid to give ethyl 3-hydroxyisoxazol-5-ylmethylsulphonylacetate. This was hydrolyzed with an alkali and treated with diphenyldiazomethane. The resulting product was then reacted with benzoyl chloride in the presence of triethylamine to give benzhydryl 3-benzoyloxyisoxazol-5-ylmethylsulphonylacetate.

Infrared absorption spectrum (Nujol) $\nu cm^{-1}$: 1770, 1740 (C=O).

Nuclear magnetic resonance spectrum (deuterated chloroform) δppm: 7.20–8.33 (multiplet, 5H, C$_6$H$_5$); 7.38 [singlet, 10H, C(C$_6$H$_5$)$_2$]; 7.00 [singlet, 1H, CH(C$_6$H$_5$)$_2$]; 6.78 (singlet, 1H, hydrogen at 4- position of isoxazole); 4.70 (singlet, 2H, —CH$_2$SO$_2$CH$_2$CO—); 4.18 (singlet, 2H, —CH$_2$SO$_2$CH$_2$CO—).

This ester was then treated with trifluoroacetic acid to give the title compound.

PREPARATION 12

(4-Chloro-3-mesyloxyisoxazol-5-yl)methylthioacetic acid

4-Chloro-3-hydroxy-5-methylisoxazole was reacted with benzenesulphonyl chloride in the presence of triethylamine to give 3-benzenesulphonyloxy-4-chloro-5-methylisoxasole, which was then reacted with N-bromosuccinimide to give 3-benzenesulphonyloxy-5-bromomethyl-4-chloroisoxazole. This was then treated by the procedure described in Preparation 10, to afford benzhydryl 4-chloro-3-hydroxyisoxazol-5-ylmethylthioacetate.

Infrared absorption spectrum (liquid film) $\nu cm^{-1}$: 1735 (C=O).

Nuclear magnetic resonance spectrum (deuterated chloroform) δppm: 7.37 [singlet, 10H, C(CH$_6$H$_5$)$_2$]; 6.95 [singlet, 1H, CH(C$_6$H$_5$)$_2$]; 3.85 (singlet, 2H, CH$_2$SCH$_2$CO); 3.37 (singlet, 5H, CH$_2$SCH$_2$CO,CH$_3$).

This ester was reacted with triethylamine and methyl chloride and the resulting product was treated with trifluoroacetic acid to give the title compound.

PREPARATION 13

4-Chloro-3-mesyloxyisoxazol-5-ylmethylsulphonylacetic acid

4-Chloro-3-hydroxyisoxazol-5-ylmethylthioacetic acid was treated by the procedure described in Preparation 11 to give the ethyl ester, which was then oxidized to the corresponding sulphone. The resulting product was hydrolyzed with an alkali and then treated with diphenyldiazomethane. The resulting benzhydryl ester was then reacted with mesyl chloride to give benzhydryl 4-chloro-3-mesyloxyisoxazol-5-ylmethylsulphonylacetate.

Infrared absorption spectrum (liquid film) $\nu cm^{-1}$: 1740 (C=O).

Nuclear magnetic resonance spectrum (deuterated chloroform) δppm: 7.42 [singlet, 10H, C(C$_6$H$_5$)$_2$]; 7.04 [singlet, 1H, CH(C$_6$H$_5$)$_2$]; 4.77 (singlet, 2H, —CH- $_2SO_2CH_2CO$); 4.20 (singlet, 2H, $CH_2SO_2C\underline{H}_2CO$); 3.45 (singlet, 3H, $CH_3$).

This ester was then treated with trifluoroacetic acid to give the title compound.

EXAMPLE 1

7β-[(3-Benzoyloxyisoxazol-5-yl)acetamido]-7α-methoxy-3-(1-methyl-1H-tetrazol-5-yl)thiomethyl-3-cephem-4-carboxylic acid (Compound No. 1)

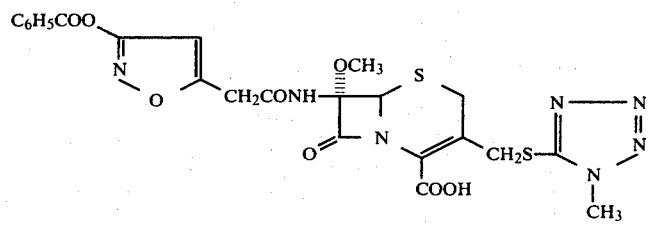

In 5 ml of methylene chloride were dissolved the (3-benzoyloxyisoxazol-5-yl)acetyl chloride which was obtained by refluxing a solution of 0.66 g of (3-benzoyloxyisoxazol-5-yl)acetic acid in 10 ml of thionyl chloride for 3 hours and then distilling off the excess thionyl chloride. This methylene chloride solution was added dropwise to a solution of 1.05 g of benzhydryl 7β-amino-7α-methoxy-3-(1-methyl-1H-tetrazol-5-yl)thiomethyl-3-cephem-4-carboxylate and 0.40 g of N,N-diethylaniline in 10 ml of methylene chloride, with ice-cooling. The reaction mixture was stirred in a ice bath for 30 minutes, and then the solvent was distilled off. The residue was adsorbed on 20 g of silica gel in a chromatography column, from which 1.30 g (yield 87%) of the benzhydryl ester of Compound No. 1 were obtained by elution with ethyl acetate.

This ester (1.30 g) was dissolved in a mixture of 5 ml of methylene chloride and 2.5 ml of anisole; 5 ml of trifluoroacetic acid were then added, with ice-cooling, and the mixture was stirred for 1 hour. 70 ml of diisopropyl ether were then added to the reaction mixture and the crude crystals which precipitated were collected by filtration and dissolved in 3 ml of methylene chloride. To this solution were added 50 ml of diethyl ether to give 1.00 g (yield 100%) of crystals of the desired Compound No. 1.

Infrared absorption spectrum (Nujol - Trade Mark) $vcm^{-1}$: 1780 (β-lactam C=O).

Nuclear magnetic resonance spectrum (deuterated dimethyl sulphoxide) δppm: 6.62 (singlet, 1H, hydrogen at 4- position of isoxazole); 5.11 (singlet, 1H, 6-cephem hydrogen); 4.27 (AB- type quartet, 2H, J=13.0 Hz, 3-cephem $CH_2$); 3.96 (singlet, 2H, $CH_2CO$); 3.90 (singlet, 3H, N—$CH_3$); 3.59 (AB- type quartet, 2H, J=18.0 Hz, 2-cephem $H_2$); 3.40 (singlet, 3H, $OCH_3$).

EXAMPLE 2

7β-[(3-Hydroxyisoxazol-5-yl)acetamido]-7α-methoxy-3-(1-methyl-1H-tetrazol-5-yl)thiomethyl-3-cephem-4-carboxylic acid (Compound No. 2)

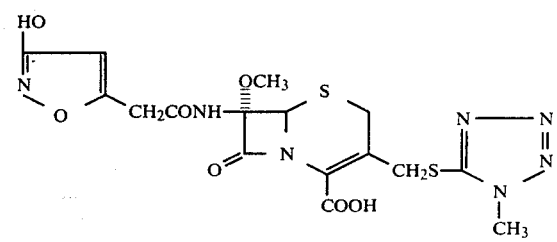

0.746 g of 7β-[(3-benzoyloxyisoxazol-5-yl)acetamido]-7α-methoxy-3-(1-methyl-1H-tetrazol-5-yl)thiomethyl-3-cephem-4-carboxylic acid was dissolved in 50% v/v aqueous ethanol. The mixture was stirred for 3 hours at room temperature whilst maintaining the pH at a value of 8.0–8.5 by addition of 3% w/v aqueous ammonia. The solvent was then distilled under reduced pressure from the reaction mixture and the residue was washed with 15 ml of acetone and then added to 5 ml of water. 20 ml of ethyl acetate were then added to the mixture, followed by concentrated hydrochloric acid to adjust the pH of the aqueous layer to a value of 1.9. The ethyl acetate layer was separated off and the solvent was distilled off under reduced pressure. 20 ml of diisopropyl ether were added to the residue, to give 0.425 g of crystals of the desired Compound No. 2.

Infrared absorption spectrum (Nujol) $vcm^{-1}$: 1779 (β-lactam C=O);

Nuclear magnetic resonance spectrum (deuterated dimethyl sulphoxide) δppm: 5.93 (singlet, 1H, 4- isoxazole hydrogen); 5.15 (singlet, 1H, 6- cephem hydrogen); 4.33 (AB- type quartet, 2H, J=13.0 Hz, 3-cephem $CH_2$); 3.97 (AB- type quartet, 3H, N-$CH_3$); 3.77 (singlet, 2H, $CH_2CO$); 3.60 (AB- type quartet, 2H, J=18.0 Hz, 2-cephem $H_2$); 3.45 (singlet, 3H, $OCH_3$).

EXAMPLE 3

7α-Methoxy-7β-[(3-methoxyisoxazol-5-yl)acetamido]-3-(1-methyl-1H-tetrazol-5-yl)thiomethyl-3-cephem-4-carboxylic acid (Compound No. 3)

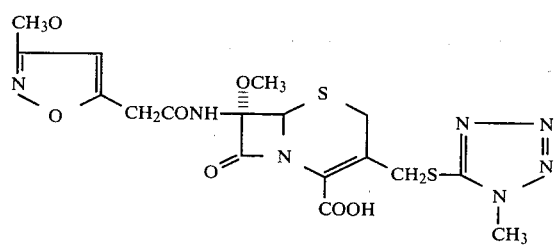

In 3 ml of methylene chloride were dissolved (3-methoxyisoxazol-5-yl)acetyl chloride, which had been obtained by refluxing a solution of 0.31 g of (3-methoxyisoxazol-5-yl)acetic acid in 5 ml of thionyl chloride for 1.5 hours and then distilling off the excess thionyl chloride. The methylene chloride solution was added dropwise to a solution of 0.52 g of benzhydryl 7β-amino-7α-methoxy-3-(1-methyl-1H-tetrazol-5-yl)thiomethyl-3-cephem-4-carboxylate and 0.30 g of N,N-diethylaniline in 10 ml of methylene chloride, with ice-cooling. The reaction mixture was then stirred in an ice bath for 30 minutes and then the solvent was distilled off under reduced pressure. The residue was adsorbed on a preparative thin layer chromatograph and developed by a 3:1 by volume mixture of benzene and ethyl acetate, to give 0.57 g (86%) of the benzhydryl ester of the desired Compound No. 3 from the portion having an Rf value of 0.25.

0.40 g of this ester was dissolved in a mixture of 2 ml of methylene chloride and 0.5 ml of anisole; 2 ml of trifluoroacetic acid were added to the solution under ice-cooling and then the mixture was stirred for 1.5 hours. At the end of this time, 80 ml of diisopropyl ether were added to the reaction mixture to give 0.29 g (97%) of crystals of the desired Compound No. 3.

Infrared absorption spectrum (Nujol) νcm$^{-1}$: 1778 (β-lactam C=O).

Nuclear magnetic resonance spectrum (deuterated dimethyl sulphoxide) δppm: 6.12 (singlet, 1H, 4-isoxazole H); 5.15 (singlet, 1H, 6-cephem H); 4.35 (AB- type quartet, 2H, J=13.0 Hz, 3-cephem CH$_2$); 3.98 (singlet, 3H, 3-isoxazole OCH$_3$); 3.92 (singlet, 3H, N-CH$_3$); 3.83 (singlet, 2H, CH$_2$CO); 3.65 (AB-type quartet, 2H, J=18.0 Hz, 2-cephem H$_2$); 3.45 (singlet, 3H, 7α-OCH$_3$).

EXAMPLE 4

3-Acetoxymethyl-7β-[(3-benzoyloxyisoxazol-5-yl)acetamido]-7α-methoxy-3-cephem-4-carboxylic acid (Compound No. 4)

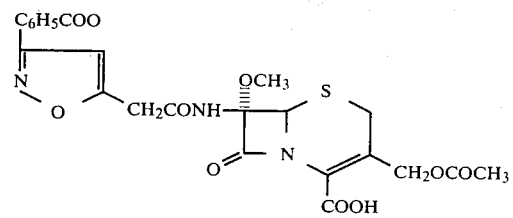

0.59 g of sodium (3-benzoyloxyisoxazol-5-yl)acetate was suspended in 5 ml of methylene chloride, and 0.37 ml of oxalyl chloride were then added, with ice-cooling. After adding one drop of N,N-dimethylformamide, the mixture was stirred for 30 minutes. The solvent was then distilled off under reduced pressure to give (3-benzoyloxyisoxazol-5-yl)acetyl chloride, which was then dissolved in 5 ml of methylene chloride. This solution was added dropwise to a solution of 685 mg of benzhydryl 3-acetoxymethyl-7β-amino-7α-methoxy-3-cephem-4-carboxylate and 325 mg of N,N-diethylaniline in 5 ml of methylene chloride, maintaining the internal temperature at about −10° C. After stirring the mixture at a temperature between −10° C. and −5° C. for 45 minutes, the reaction mixture was evaporated to dryness under reduced pressure and the residue was adsorbed on a silica gel preparative thin layer chromatograph and developed by a 2:1 by volume mixture of benzene and ethyl acetate. The portion having an Rf value of 0.54 was extracted to give 660 mg (64.7%) of the benzhydryl ester of the desired Compound No. 4.

650 mg of this ester were dissolved in a mixture of 2 ml of methylene chloride and 0.5 ml of anisole, and then 2.5 ml of trifluoroacetic acid were added thereto, with ice-cooling. The mixture was stirred for 1.5 hours, after which 100 ml of diisopropyl ether were added. After stirring the mixture for 30 minutes, the precipitates were collected by filtration and washed with diisopropyl ether to give 387 mg (78.0%) of the desired Compound No. 4 as a yellow powder.

Rf=0.31 (80:40:1:1 by volume mixture of chloroform, ethanol, acetic acid and water).

Infrared absorption spectrum: (Nujol) νcm$^{-1}$: 1778 (β-lactam C=O).

Nuclear Magnetic resonance spectrum (deuterated acetone) δppm: 6.26 (singlet, 1H, 4-isoxazole H); 5.20 (singlet, 1H, 6-cephem H); 5.04 (AB- type quartet, 2H, J=13.0 Hz, 3-cephem CH$_2$); 4.12 (singlet, 2H, CH$_2$CO); 3.58 (singlet, 3H, 7α-OCH$_3$); 3.50 (singlet, 2H, 2-cephem H$_2$); 2.10 (singlet, 3H, 3-cephem —CH$_2$OCOCH$_3$).

EXAMPLE 5

7β-[(3-Hydroxyisoxazol-5-yl)acetamido]-7α-methoxy-3-(5-methyl-1,3,4-thiadiazol-2-yl)thiomethyl-3-cephem-4-carboxylic acid (Compound No. 5)

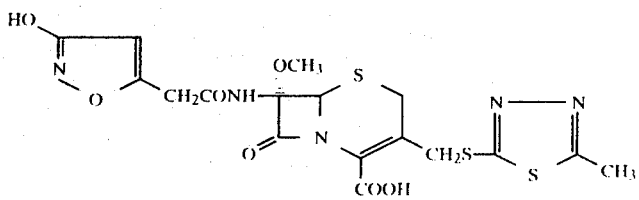

300 mg of 3-acetoxymethyl-7β-[(3-benzoyloxyisoxazol-5-yl)-acetamido]-7α-methoxy-3-cephem-4-carboxylic acid (prepared as described in Example 4), 186.4 mg of 2-mercapto-5-methyl-1,3,4-thiadiazole and 118.4 mg of sodium hydrogen carbonate were dissolved in 5 ml of a pH 7.0 phosphoric acid buffer. The solution was stirred at an internal temperature of 90° C. for 15 minutes, after which concentrated hydrochloric acid was added under ice-cooling to adjust the mixture to a pH value of 2.0. The mixture was then extracted four times, each time with 10 ml of ethyl acetate, and the combined ethyl acetate extracts were washed with water and dried over anhydrous magnesium sulphate; the solvent was then distilled off under reduced pressure. The residue was dissolved in acetone and adsorbed on a preparative thin layer chromatograph of silica gel and developed by a 8:5:1:1 by volume mixture of chloroform, ethanol, acetic acid and water. The portion having an Rf value of 0.35 was extracted with methanol. The methanol was distilled from the extract and 5 ml of water and 20 ml of ethyl acetate were added to the residue. After adjusting the pH of the mixture to a value of about 2.0 by addition of concentrated hydrochloric acid under ice-cooling, the ethyl acetate phase was separated off. The aqueous phase was extracted three times, each time with 10 ml of ethyl acetate. The ethyl acetate phase and the ethyl acetate extracts were combined and washed with water and then dried over anhydrous magnesium sulphate. The solvent was distilled off under reduced pressure, to give 200 mg (69.6%) of the desired Compound No. 5, as a pale brown powder.

Infrared absorption spectrum (Nujol) $\theta$cm$^{-1}$: 1779 (β-lactam C=O).

Nuclear magnetic resonance spectrum (deuterated acetone) δppm: 5.93 (singlet, 1H, 4-isoxazole H), 5.08 (singlet, 1H, 6-cephem H); 4.44 (AB-type quartet, 2H, J=13.0 Hz, 3-cephem CH$_2$); 3.82 (singlet, 2H, CH$_2$CO); 3.64 (doublet, 2H, 2-cephem H$_2$); 3.48 (singlet, 3H, 7α-OCH$_3$); 2.68 (singlet, 3H, CH$_3$ on thiadiazole).

EXAMPLE 6

7β-[(3-Mesyloxyisoxazol-5-yl)acetamido]-7α-methoxy-3(1-methyl-1H-tetrazol-5-yl)thiomethyl-3-cephem-4-carboxylic acid (Compound No. 10)

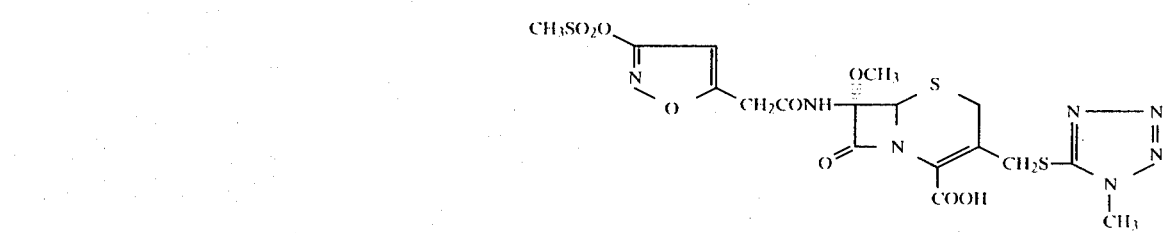

221 mg of (3-mesyloxyisoxazol-5-yl)acetic acid were dissolved in 5 ml of methylene chloride. 208 mg of phosphorus pentachloride were added thereto and the resulting mixture was stirred for 1 hour at room temperature, after which the solvent was distilled off under reduced pressure. The resulting (3mesyloxyisoxazol-5-yl)-acetyl chloride was then dissolved in 5 ml of methylene chloride. This solution was added to a solution of 262 mg of benzhydryl 7β-amino-7α-methoxy-3(1-methyl-1H-tetrazol-5-yl)thiomethyl-3-cephem-4-carboxylate and 142 mg of N,N-diethylaniline in 5 ml of methylene chloride. The reaction mixture was stirred for 10 minutes in an ice bath, after which the solvent was distilled off. The residue was dissolved in ethyl acetate and then the solution was washed with, in turn, aqueous sodium hydrogen carbonate, aqueous sodium chloride, 4% w/v hydrochloric acid and aqueous sodium chloride; the washed solution was then dried over anhydrous sodium sulphate. The solvent was distilled off and the residue was adsorbed on a preparative thin layer chromatograph of silica gel and developed with a 2:1 by volume mixture of benzene and ethyl acetate, to give 230 mg of the benzhydryl ester of the desired Compound No. 10.

220 mg of this ester were dissolved in a mixture of 1 ml of methylene chloride and 0.2 ml of anisole, and then 1 ml of trifluoroacetic acid was added thereto, with ice-cooling. After stirring the mixture for 1 hour, 50 ml of diisopropyl ether were added and the precipitates were collected by filtration to give 120 mg of the desired Compound No. 10 in the form of a white powder.

Infrared absorption spectrum (Nujol) $\nu$cm$^{-1}$: 1779 (β-lactam C=O).

Nuclear magnetic resonance spectrum (deuterated acetone) δppm: 6.63 (singlet, 1H, 4-isoxazole H); 5.27 (singlet, 1H, 6-cephem H); 4.50 (AB- type quartet, 2H, J=13.0 Hz, 3-cephem CH$_2$); 4.10 (singlet, 2H, CH$_2$CO); 4.05 (singlet, 3H, CH$_3$ on tetrazole); 3.73 (singlet, 2H, 2-cephem H$_2$); 3.47 (singlet, 3H, 7α-OCH$_3$); 3.45 (singlet, 3H, CH$_3$SO$_2$).

EXAMPLE 7

3-Carbamoyloxymethyl-7α-methoxy-7β-[(3-methoxyisoxazol-5-yl)acetamido]-3-cephem-4-carboxylic acid (Compound No. 8)

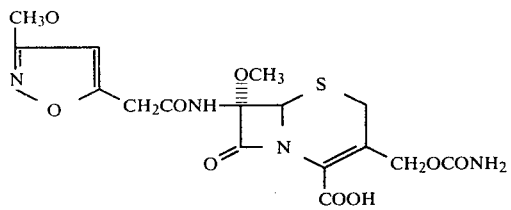

A mixture of 466 mg of dibenzhydryl N-tosylcephamycin C, 1 g of Molecular Sieve 4A, 7 ml of 1,2-dichloroethane and 350 mg of (3-methoxyisoxazol-5-yl)acetyl chloride was heated at 75° C. for 30 hours. The insolubles were filtered off and then the solvent was distilled from the filtrate under reduced pressure. The residue was adsorbed on a silica gel preparative thin layer chromatograph and developed by a 1:2 by volume mixture of benzene and ethyl acetate, to give 250 mg of the benzhydryl ester of the desired Compound No. 8.

200 mg of this ester were dissolved in a mixture of 1 ml of methylene chloride and 0.1 ml of anisole, and then 1 ml of trifluoroacetic acid was added dropwise to the solution, with ice-cooling. After stirring the solution for 1 hour, 100 ml of diisopropyl ether were added and the precipitates produced were collected by filtration, washed with diethyl ether and then dried to give 110 mg of Compound No. 8.

Infrared absorption spectrum (Nujol) $\nu cm^{-1}$: 1778 (β-lactam C=O)

Nuclear magnetic resonance spectrum (deuterated acetone) δppm: 6.10 (singlet, 1H, 4-isoxazole H); 5.20 (singlet, 1H, 6-cephem H); 5.02 (AB- type quartet, 2H, J=14.0 Hz, 3-cephem $CH_2$); 3.97 (singlet, 3H, 3-isoxazole $OCH_3$). 3.94 (singlet, 2H, $CH_2CO$); 3.56 (singlet, 3H, 7α-$OCH_3$); 3.50 (AB-type quartet, 2H, J=17.0 Hz, 2-cephem $CH_2$).

EXAMPLE 8

7β-[(3-Benzoyloxyisoxazol-5-yl)acetamido]-3-carbamoyloxymethyl-7α-methoxy-3-cephem-4-carboxylic acid (Compound No. 13)

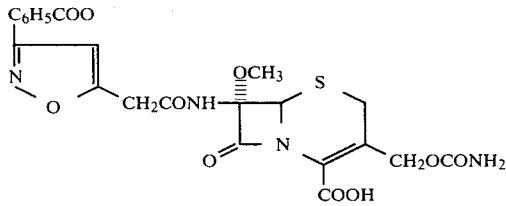

To a solution of 700 mg of dibenzhydryl N-tosylcephamycin C and 500 mg of (3-benzoyloxyisoxazol-5-yl)acetyl chloride in 15 ml of 1,2-dichloroethane were added 1.5 g of Molecular Sieve 4A, and then the mixture was stirred at 75° C. in an oil bath for 20 hours. The reaction mixture was then filtered through a Celite (Trade Mark) mineral filter, and then 150 ml of ethyl acetate were added to the filtrate. The mixture was washed with, in turn, aqueous sodium hydrogen carbonate and water, and dried over anhydrous magnesium sulphate. The solvent was then distilled off under reduced pressure and the residue was dissolved in ethyl acetate and adsorbed on a silica gel preparative thin layer chromatograph and developed by a 1:1 by volume mixture of benzene and ethyl acetate. The portion having an Rf value of 0.47 was extracted with ethyl acetate and the solvent was distilled under reduced pressure from the extract to give 400 mg (75%) of the benzhydryl ester of the desired Compound No. 13.

400 mg of this ester were dissolved in a mixture of 2 ml of methylene chloride and 0.5 ml of anisole, and then 2 ml of trifluoroacetic acid were added dropwise to the solution, with ice-cooling. After stirring the mixture for 1 hour, it was concentrated to one-third of its original volume. 100 ml of diisopropyl ether were added to the concentrated mixture and the precipitates which formed were collected by filtration. These precipitates were adsorbed on a silica gel preparative thin layer chromatograph and developed by a 8:5:1:1 by volume mixture of chloroform, ethanol, water and acetic acid to give 250 mg (82%) of the desired Compound No. 13 from the portion having an Rf value of 0.26.

Infrared absorption spectrum (Nujol) $\nu cm^{-1}$. 1779 (β-lactam C=O).

Nuclear magnetic resonance spectrum (deuterated acetone) δppm: 7.60–8.40 (multiplet, 5H, $C_6H_5CO$); 6.72 (singlet, 1H, 4-isoxazole H); 5.16 (singlet, 1H, 6-cephem H); 4.98 (AB- type quartet, 2H, J=14.0 Hz, 3-cephem $CH_2$); 4.08 (singlet, 2H, $CH_2CO$); 3.54 (singlet, 3H, 7α-$OCH_3$); 3.48 (AB- type quartet, 2H, J=18.0 Hz, 2-cephem $H_2$).

EXAMPLE 9

3-Carbamoyloxymethyl-7β-[(3-mesyloxyisoxazol-5-yl)acetamido]-7α-methoxy-3-cephem-4-carboxylic acid (Compound No. 14)

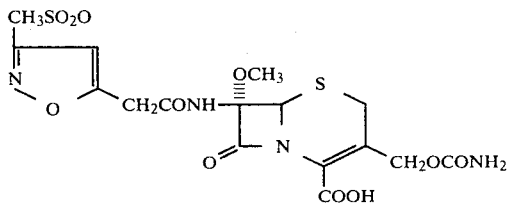

To a solution of 513 mg of dibenzhydryl N-tosylcephamycin C and 432 mg of (3-mesyloxyisoxazol-5-yl)acetyl chloride in 10 ml of 1,2-dichloroethane were added 1.1 g of Molecular Sieve 4A, and then the mixture was stirred at 75° C. in an oil bath for 27 hours. The reaction mixture was then filtered through a Celite (Trade Mark) mineral filter and 100 ml of ethyl acetate were added to the filtrate. This mixture was washed with, in turn, aqueous sodium hydrogen carbonate and water and then dried over anhydrous magnesium sulphate. The solvent was distilled off under reduced pressure and the residue was dissolved in ethyl acetate, adsorbed on a silica gel preparative thin layer chromatograph and developed by a 1:2 by volume mixture of benzene and ethyl acetate. The portion having an Rf value of 0.42 was extracted with ethyl acetate. The solvent was distilled under reduced pressure from the extract to give 73 mg (19.8%) of the benzhydryl ester of the desired Compound No. 14.

70 mg of this ester were dissolved in a mixture of 2 ml of methylene chloride and 0.2 ml of anisole, and then 1 ml of trifluoroacetic acid were added dropwise thereto, with ice-cooling. After stirring the mixture for 1 hour, the solution was concentrated to one-third of its original volume by evaporation under reduced pressure. After addition of 100 ml of diisopropyl ether to the concentrated solution, the crystals which precipitated were collected by filtration and adsorbed on a silica gel preparative thin layer chromatograph and developed by a 8:5:1:1 by volume mixture of chloroform, ethanol, acetic acid and water. 21.6 mg (41.1%) of the desired Compound No. 14 were obtained from the portion having an Rf value of 0.19.

Infrared absorption spectrum (Nujol) νcm$^{-1}$: 1779 (β-lactam C=O).

Nuclear magnetic resonance spectrum (deuterated acetone) δppm: 6.52 (singlet, 1H, 4-isoxazole H); 5.12 (singlet, 1H, 6-cephem H), 4.90 (AB- type doublet, 2H, J=13.0 Hz, 3-cephem CH$_2$); 4.07 (singlet, 2H, CH$_2$CO); 3.52 (singlet, 8H, CH$_3$SO$_2$, 7α-OCH$_3$, 2-cephem H$_2$).

EXAMPLE 10

7β-[(3-Ethanesulphonyloxyisoxazol-5-yl)acetamido]-7α-methoxy-3-(1-methyl-1H-tetrazol-5-yl)thiomethyl-3-cephem-4-carboxylic acid (Compound No. 15)

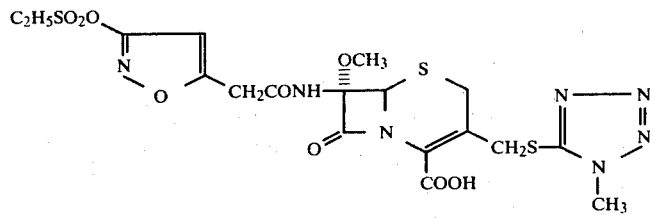

650 mg of (3-ethanesulphonyloxyisoxazol-5-yl)acetic acid were dissolved in 7 ml of methylene chloride, 577 mg of phosphorus pentachloride were added thereto, and the mixture was stirred at room temperature for 1 hour. The solvent was distilled off and the residual (3-ethanesulphonyloxyisoxazol-5-yl)acetyl chloride thus obtained was dissolved in 5 ml of methylene chloride. This solution was added to a solution of 300 mg of benzhydryl 7β-amino-7α-methoxy-3-(1-methyl-1H-tetrazol-5-yl)thiomethyl-3-cephem-4-carboxylate and 207 mg of N,N-diethylaniline in 4 ml of methylene chloride. The reaction mixture was stirred in an ice bath for 1 hour and then the solvent was distilled off. The residue was dissolved in ethyl acetate and the solution was washed with, in turn, dilute aqueous potassium bisulphate, aqueous sodium chloride, aqueous sodium hydrogen carbonate and aqueous sodium chloride, and then dried over anhydrous magnesium sulphate. The solvent was distilled off and the residue was adsorbed on a silica gel preparative thin layer chromatograph and developed with a 1:1 by volume mixture of benzene and ethyl acetate. The portion having an Rf value of 0.63 was extracted with ethyl acetate. The solvent was distilled under reduced pressure from the extract to give 422 mg (100%) of the benzhydryl ester of the desired Compound No. 15.

410 mg of this ester were dissolved in a mixture of 4 ml of methylene chloride and 0.2 ml of anisole, and 2 ml of trifluoroacetic acid were added therefore, with ice-cooling. After stirring the mixture for 1 hour, 100 ml of diisopropyl ether were added. The crystals which precipitated were collected by filtration and adsorbed on a silica gel preparative thin layer chromatograph and developed by a 4:1:1 by volume mixture of n-butanol, acetic acid and water. 280 mg (88.0%) of the desired Compound No. 15 were obtained from the portion having an Rf value of 0.34.

Infrared absorption spectrum (Nujol) νcm$^{-1}$: 1780 (β-lactam C=O).

Nuclear magnetic resonance spectrum (deuterated acetone) δppm: 6.56 (singlet, 1H, 4-isoxazole H); 5.10 (singlet, 1H, 6-cephem H); 4.57 (AB- type quartet, 2H, J=13 Hz, 3-cephem CH$_2$); 4.07 (singlet, 2H, CH$_2$CO); 4.02 (singlet, 3H, CH$_3$ on heterozole); 3.71 (singlet, 2H, 2-cephem H$_2$); 3.60 (quartet, 2H, J=7.5 Hz, CH$_3$CH$_2$SO$_2$); 3.52 (singlet, 3H, 7α-OCH$_3$); 1.50 (triplet, 3H, J=7.5 Hz, CH$_3$CH$_2$SO$_2$).

EXAMPLE 11

7β-[(3-Benzenesulphonyloxyisoxazol-5-yl)acetamido]-7α-methoxy-3-(1-methyl-1H-tetrazol-5-yl)thiomethyl-3-cephem-4-carboxylic acid (Compound No. 21)

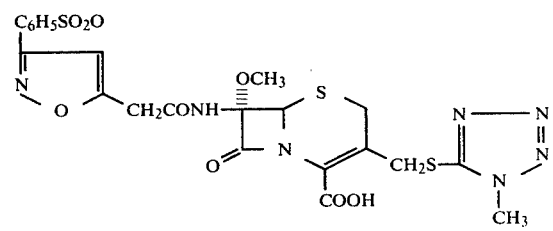

300 mg of (3-benzenesulphonyloxyisoxazol-5-yl)acetic acid were dissolved in 4 ml of methylene chloride; 229 mg of phosphorus pentachloride were added thereto and the mixture was stirred at room temperature for 1.5 hours, after which the solvent was distilled off under reduced pressure. The resulting (3-benzene-sulphonyloxyisoxazol-5-yl)acetyl chloride was then dissolved in 3 ml of methylene chloride and the resulting solution was added to a solution of 262 mg of benzhydryl 7β-amino-7α-methoxy-3-(1-methyl-1H-tetrazol-5-yl)thiomethyl-3-cephem-4-carboxylate and 164 mg of N,N-diethylaniline in 5 ml of methylene chloride. After stirring the reaction mixture in an ice bath for 1 hour, the solvent was distilled off and the residue was dissolved in ethyl acetate. The solution was then washed with, in turn, dilute aqueous potassium bisulphate, aqueous sodium chloride, aqueous sodium hydrogen carbonate and aqueous sodium chloride; the solution was then dried over anhydrous magnesium sulphate. The solvent was then distilled off to give 394 mg (100%) of the benzhydryl ester of the desired Compound No. 21.

390 mg of this ester were dissolved in a mixture of 4 ml of methylene chloride and 0.4 ml of anisole, and then 2 ml of trifluoroacetic acid were added thereto, with ice-cooling. After stirring the mixture for 1 hour, 100 ml of diisopropyl ether were added to the solution. The crystals which precipitated were collected by filtration and adsorbed on a silica gel preparative thin layer chromatograph and developed by a 4:1:1 by volume mixture of n-butanol, acetic acid and water. 188 mg (61%) of the desired Compound No. 21 were obtained from the portion having an Rf value of 0.53.

Infrared absorption spectrum (Nujol) $\nu$cm$^{-1}$: 1779 ($\beta$-lactam C=O).

Nuclear magnetic resonance spectrum (deuterated acetone) $\delta$ppm: 8.20–7.70 (multiplet, 5H, C$_6$H$_5$SO$_2$); 6.46 (singlet, 1H, 4-isoxazole H); 5.18 (singlet, 1H, 6-cephem H); 4.52 (singlet, 2H, 3-cephem CH$_2$); 4.06 (singlet, 5H, CH$_3$ on tetrazole, CH$_2$CO); 3.76 (singlet, 2H, 2-cephem H$_2$); 3.57 (singlet, 3H, 7$\alpha$-OCH$_3$).

EXAMPLE 12

7$\beta$-[(4-Chloro-3-mesyloxyisoxazol-5-yl)acetamido]-7$\alpha$-methoxy-3-(1-methyl-1H-tetrazol-5-yl)thiomethyl-3-cephem-4-carboxylic acid (Compound No. 22)

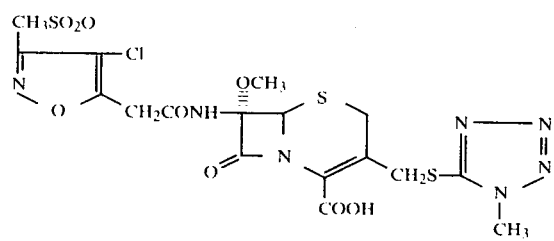

662 mg of (4-chloro-3-mesyloxyisoxazol-5-yl)acetic acid were dissolved in 5 ml of methylene chloride; 450 mg of phosphorus pentachloride were added and the resulting mixture was stirred at room temperature for 1 hour, after which the solvent was distilled off under reduced pressure. The resulting (4-chloro-3-mesyloxyisoxazol-5-yl)acetyl chloride was dissolved in 2 ml of methylene chloride and then this solution was added to a solution of 400 mg of benzhydryl 7$\beta$-amino-7$\alpha$-methoxy-3-(1-methyl-1H-tetrazol-5-yl)-thiomethyl-3-cephem-4-carboxylate and 320 mg of N,N-diethylaniline in 5 ml of methylene chloride. After stirring the reaction mixture in an ice bath for 45 minutes, the solvent was distilled off and the residue was dissolved in ethyl acetate. The resulting solution was washed with, in turn, dilute aqueous potassium bisulphate, aqueous sodium chloride, aqueous sodium hydrogen carbonate and aqueous sodium chloride and then dried over anhydrous magnesium sulphate. The solvent was distilled off and the residue was adsorbed on a silica gel preparative thin layer chromatograph and developed with a 1:1 by volume mixture of benzene and ethyl acetate to give 480 mg (82.6%) of the benzhydryl ester of the desired Compound No. 22.

424 mg of this ester were dissolved in a mixture of 2 ml of methylene chloride and 0.4 ml of anisole, and then 2 ml of trifluoroacetic acid were added thereto, with ice-cooling. After stirring the mixture for 45 minutes, 100 ml of diisopropyl ether were added and the crystals which precipitated were collected by filtration and adsorbed on a silica gel preparative thin layer chromatograph and developed by a 8:5:1:1 by volume mixture of chloroform, ethanol, acetic acid and water. There were obtained 193 mg (58.3%) of the desired Compound No. 22 from the portion having an Rf value of 0.50.

Infrared absorption spectrum (Nujol)$\nu$cm$^{-1}$: 1780 ($\beta$-lactam C=O).

Nuclear magnetic resonance spectrum (deuterated acetone) $\beta$ppm: 5.14 (singlet, 1H, 6-cephem H); 4.49 (singlet, 2H, 3-cephem CH$_2$); 4.18 (singlet, 2H, CH$_2$CO); 4.02 (singlet, 3H, CH$_3$ on tetrazole); 3.67 (singlet, 5H, 2-cephem H$_2$,7$\alpha$-OCH$_3$); 3.57 (singlet, 3H, CH$_3$SO$_2$).

EXAMPLE 13

7$\beta$-[(4-Chloro-3-hydroxyisoxazol-5-yl)acetamido]-7$\alpha$-methoxy-3-(1-methyl-1H-tetrazol-5-yl)thiomethyl-3-cephem-4-carboxylic acid (Compound No. 7)

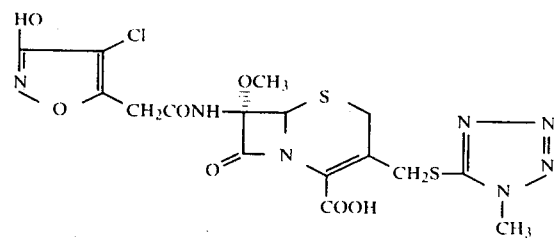

1 ml of a saturated aqueous sodium hydrogen carbonate solution containing 60 mg of 7$\beta$-[(4-chloro-3-mesyloxyisoxazol-5-yl)-aacetamido]-7$\alpha$-methoxy-3-(1-methyl-1H-tetrazol-5-yl)thiomethyl-3-cephem-4-carboxylic acid (prepared as described in Example No. 12) was stirred at room temperature for 30 minutes and then its pH was adjusted to a value of 2.0 by addition of 3N hydrochloric acid, after which it was extracted three times, each with 10 ml of ethyl acetate. The combined ethyl acetate extracts were washed with water and dried over anhydrous magnesium sulphate, after which the solvent was distilled off under reduced pressure. The residue was adsorbed on a silica gel preparative thin layer chromatograph and developed by a 8:5:1:1 by volume mixture of chloroform, ethanol, acetic acid and water. 41 mg (78.8%) of the desired Compound No. 7 were obtained from the portion having an Rf value of 0.22.

Infrared absorption spectrum (Nujol)$\nu$cm$^{-1}$: 1779 ($\beta$-lactam C=O).

Nuclear magnetic resonance spectrum (deuterated acetone) $\delta$ppm: 5.14 (singlet, 1H, 6-cephem H); 4.50 (singlet, 2H, 3-cephem CH$_2$); 4.04 (singlet, 3H, CH$_3$ on tetrazole); 3.98 (singlet, 2H, CH$_2$CO); 3.72 (singlet, 2H, 2-cephem H$_2$); 3.54 (singlet, 3H, 7$\alpha$-OCH$_3$).

EXAMPLE 14

7$\beta$-[(4-Bromo-3-mesyloxyisoxazol-5-yl)acetamido]-7$\alpha$-methoxy-3-(1-methyl-1H-tetrazol-5-yl)thiomethyl-3-cephem-4-carboxylic acid (Compound No. 24)

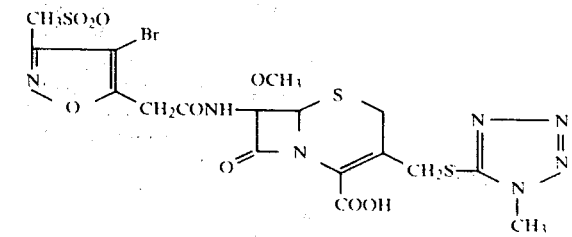

300 mg of (4-bromo-3-mesyloxyisoxazol-5-yl)acetic acid were dissolved in 5 ml of methylene chloride; 208 mg of phosphorus pentachloride were added thereto and the mixture was stirred at room temperature for 1 hour, after which the solvent was distilled off under reduced pressure. The resulting (4-bromo-3-mesyloxyisoxazol-5-yl)acetyl chloride was dissolved in 2 ml of methylene chloride, and this solution was added to a solution of 400 mg of benzhydryl 7β-amino-7α-methoxy-3-(1-methyl-1H-tetrazol-5-yl)thiomethyl-3-cephem-4-carboxylate and 149 mg of N,N-diethylaniline in 4 ml of methylene chloride. After stirring the reaction mixture in an ice bath for 1 hour, the solvent was distilled off and the residue was dissolved in ethyl acetate. This solution was washed with, in turn, dilute aqueous potassium bisulphate, aqueous sodium chloride, aqueous sodium hydrogen carbonate and aqueous sodium chloride and then dried over anhydrous magnesium sulphate, after which the solvent was distilled off. The residue was adsorbed on a silica gel preparative thin layer chromatograph and developed with a 1:1 by volume mixture of benzene and ethyl acetate, to give 532 mg (86.8%) of the benzhydryl ester of the desired Compound No. 24 from the portion having an Rf value of 0.52.

477 mg of this ester were dissolved in a mixture of 2.5 ml of methylene chloride and 0.5 ml of anisole, and then 2.5 ml of trifluoroacetic acid were added thereto, with ice-cooling. After stirring the mixture for 1 hour, 100 ml of diisopropyl ether were added and the crystals which precipitated were collected by filtration and then adsorbed on a silica gel preparative thin layer chromatograph and developed with a 8:5:1:1 by volume mixture of chloroform, ethanol, acetic acid and water. There were obtained 311 mg (82.3%) of the desired Compound No. 24 from that portion having an Rf value of 0.46.

Infrared absorption spectrum (Nujol) νcm$^{-1}$: 1779 (β-lactam C=O).

Nuclear magnetic resonance spectrum (deuterated acetone) δppm: 5.19 (singlet, 1H, 6-cephem H); 4.43 (AB-type quartet, 2H, J=13.0 Hz, 3-cephem CH$_2$); 4.13 (singlet, 2H, CH$_2$CO); 4.00 (singlet, 3H, CH$_3$ on tetrazole); 3.62 (singlet, 5H, 7α-OCH$_3$, 2-cephem H$_2$); 3.52 (singlet, 3H, CH$_3$SO$_2$).

EXAMPLE 15

7β-[(4-Bromo-3-hydroxyisoxazol-5-yl)acetamido]-7α-methoxy-3-(1-methyl-1H-tetrazol-5-yl)thiomethyl-3-cephem-4-carboxylic acid (Compound No. 6)

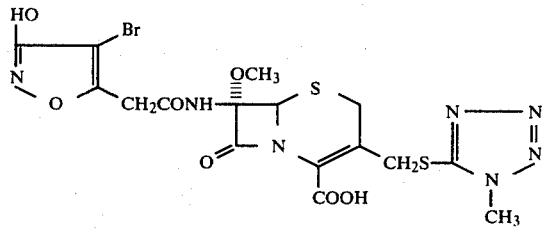

2 ml of a saturated aqueous sodium hydrogen carbonate solution containing 100 mg of 7β-[(4-bromo-3-mesyloxyisoxazol-5-yl)acetamido]-7α-methoxy-3-(1-methyl-1H-tetrazol-5-yl)thiomethyl-3-cephem-4-carboxylic acid (prepared as described in Example 14) was allowed to dissolve at room temperature for 20 minutes, after which its pH value was adjusted to 2.0 by the addition of 3N hydrochloric acid, and then the solution was extracted three times, each with 10 ml of ethyl acetate. The combined ethyl acetate extracts were washed with water and dried over anhydrous magnesium sulphate, after which the solvent was distilled off under reduced pressure and the residue was adsorbed on a silica gel preparative thin layer chromatograph and developed by a 8:5:1:1 by volume mixture of chloroform, ethanol, acetic acid and water. 80 mg (91%) of the desired Compound No. 6 were obtained from the portion having an Rf value of 0.30.

Infrared absorption spectrum (Nujol) νcm$^{-1}$: 1780 (β-lactam C=O).

Nuclear magnetic resonance spectrum (deuterated acetone) δppm: 5.08 (singlet, 1H, 6-cephem H); 4.42 (singlet, 2H, 3-cephem CH$_2$); 4.00 (singlet, 3H, CH$_3$ on tetrazole); 3.96 (singlet, 2H, CH$_2$CO); 3.69 (singlet, 2H, 2-cephem H$_2$); 3.52 (singlet, 3H, 7α-OCH$_3$).

EXAMPLE 16

7β-[(3-Mesyloxy-4-methoxycarbonylisoxazol-5-yl)acetamido]-7α-methoxy-3-(1-methyl-1H-tetrazol-5-yl)thiomethyl-3-cephem-4-carboxylic acid (Compound No. 27)

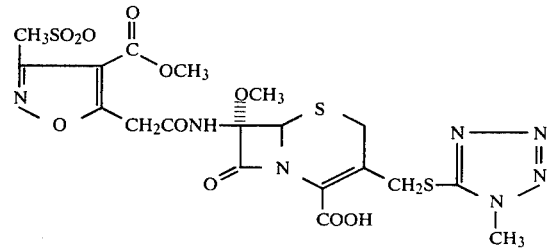

558 mg of (3-mesyloxy-4-methoxycarbonylisoxazol-5-yl)-acetic acid were dissolved in 10 ml of methylene chloride; 416 mg of phosphorus pentachloride were added under ice-cooling, the mixture was stirred for 1 hour and then the solvent was distilled off. The resulting (3-mesyloxy-4-methoxycarbonylisoxazol-5-yl)-acetyl chloride was dissolved in 10 ml of methylene chloride and then this solution was added to a solution of 525 mg of benzhydryl 7β-amino-7α-methoxy-3-(1-methyl-1H-tetrazol-5-yl)thiomethyl-3-cephem-4-carboxylate and 298 mg of N,N-diethylaniline in 20 ml of methylene chloride. The reaction mixture was stirred in an ice bath for 2 hours, after which the solvent was distilled off and the residue was dissolved in ethyl acetate. The solution was washed with water and dried and then the solvent was distilled off to give 786 mg (100%) of the benzhydryl ester of the desired Compound No. 27.

786 mg of this ester were dissolved in a mixture of 2 ml methylene chloride and 1 ml of anisole, and then 2 ml of trifluoroacetic acid were added thereto, with ice-cooling. The solution was stirred for 2 hours, and then 50 ml of diisopropyl ether were added to the solution. The precipitate produced was collected by filtration, adsorbed on a silica gel preparative thin layer chromatograph and developed by a 8:5:1:1 by volume mixture of chloroform, ethanol, acetic acid and water to give 620 mg (100%) of Compound No. 27.

Infrared absorption spectrum (Nujol) νcm$^{-1}$: 1778 (β-lactam C=O).

Nuclear magnetic resonance spectrum (deuterated acetone) δppm: 5.10 (singlet, 1H, 6-cephem H); 4.43 (singlet, 4H, CH$_2$CO, 3-cephem CH$_2$); 4.05 (singlet, 3H, CH$_3$ on tetrazole); 3.90 (singlet, 3H, COOCH$_3$); 3.72 (singlet, 2H, 2-cephem H$_2$); 3.65 (singlet, 3H, 7α-OCH$_3$); 3.60 (singlet, 3H, CH$_3$SO$_2$).

EXAMPLE 17

7β-[(3-Hydroxy-4-methoxycarbonylisoxazol-5-yl)acetamido]-7α-methoxy-3-(1-methyl-1H-tetrazol-5-yl)thiomethyl-3-cephem-4-carboxylic acid. (Compound No. 28).

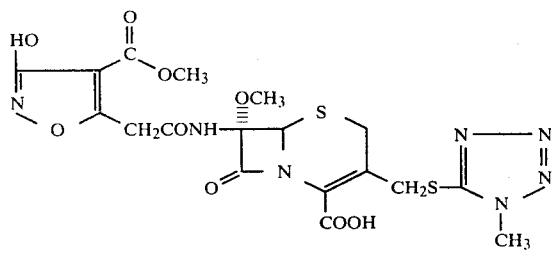

A solution of 427 mg of 7β-[(3-mesyloxy-4-methoxycarbonylisoxazol-5-yl)acetamido]-7α-methoxy-3-(1-methyl-1H-tetrazol-5-yl)-thiomethyl-3-cephem-4-carboxylic acid in 5 ml of acetone and 5 ml of water was stirred for 3 hours, whilst maintaining the pH at a value from 8.5 to 9.0 by the addition of 1N aqueous ammonia. The pH of the solution was then adjusted to a value of 7.0 and the solvent was distilled off. After adjusting the residue to a pH of 2.0, it was extracted with ethyl acetate; the extract was dried and the solvent was distilled off. The residue was adsorbed on a silica gel preparative thin layer chromatograph and developed by a 8:5:1:1 by volume mixture of chloroform, ethanol, acetic acid and water to give 190 mg (51%) of the desired compound No. 28.

Infra-red absorption spectrum (Nujol) $\nu$ cm$^{-1}$. 1779 (β-lactam C=O)

Nuclear magnetic resonance spectrum (deuterated acetone) δ ppm: 5.40 (singlet, 1H, 6-cephem H); 4.42 (singlet, 2H, 3-cephem CH$_2$); 4.18 (singlet, 2H, CH$_2$CO); 3.99 (singlet, 3H,CH$_3$ on tetrazole); 3.85 (singlet, 3H, COOCH$_3$); 3.66 (singlet, 2H, 2-cephem H$_2$); 3.51 (singlet, 3H, 7α-OCH$_3$).

EXAMPLE 18

7β-[(3-Benzenesulphonyloxyisoxazol-5-yl)methylthioacetamido]-7α-methoxy-3-(1-methyl-1H-tetrazol-5-yl)thiomethyl-3-cephem-4-carboxylic acid. (Compound No. 39).

329 mg of (3-benzenesulphonyloxyisoxazol-5-yl)thiomethylacetic acid were dissolved in 10 ml of methylene chloride, 208 mg of phosphorus pentachloride were added to the solution and the mixture was stirred at room temperature for 1 hour, after which the solvent was distilled off under reduced pressure. The resulting (3-benzenesulphonyloxyisoxazol-5-yl)methylthioacetyl chloride was dissolved in 10 ml of methylene chloride and the solution was added to a solution of 315 mg of benzhydryl 7β-amino-7α-methoxy-3-(1-methyl-1H-tetrazol-5-yl)-thiomethyl-3-cephem-4-carboxylate and 149 mg of N,N-diethylaniline in 10 ml of methylene chloride. This reaction mixture was stirred for 1 hour in an ice bath, after which the solvent was distilled off and the residue was dissolved in ethyl acetate, washed with, in turn, aqueous sodium chloride, dilute aqueous potassium hydrogen sulphate, aqueous sodium hydrogen carbonate and aqueous sodium chloride, and then dried. The solvent was distilled off to give 500 mg (99.6%) of the benzhydryl ester of the desired Compound No. 39.

500 mg of this ester were dissolved in a mixture of 2 ml of methylene chloride and 0.2 ml of anisole, and then 2 ml of trifluoroacetic acid were added, with ice-cooling, to the solution and stirred for 1 hour. At the end of this time, 100 ml of diisopropyl ether were added and the precipitates which formed were collected by filtration, adsorbed on a silica gel preparative thin layer chromatograph and developed by a 16:10:1:1 by volume mixture of chloroform, alcohol, acetic acid and water, to give 120 mg (29.9%) of the desired Compound No. 39.

Infra-red absorption spectrum (Nujol) $\nu$ cm$^{-1}$: 1780 (β-lactam C=O).

Nuclear magnetic resonance spectrum (deuterated acetone) δ ppm: 7.80–8.25 (multiplet, 5H, C$_6$H$_5$); 6.50 (singlet, 1H, 4-isoxazole H); 5.18 (singlet, 1H, 6-cephem H); 4.50 (AB-type quartet, 2H, J=13.5 Hz,3-cephem CH$_2$); 4.10 (singlet, 2H, CH$_2$SCH$_2$CO); 4.03 (singlet, 3H, CH$_3$ on tetrazole); 3.77 (AB-type quartet, 2H, J=18.0 Hz, 2-cephem H$_2$); 3.55 (singlet, 3H, 7α-OCH$_3$); 3.43 (singlet, 2H, CH$_2$SCH$_2$CO).

EXAMPLE 19

7β-[(3-Hydroxyisoxazol-5-yl)methylthioacetamido]-7α-methoxy-3-(1-methyl-1H-tetrazol-5-yl)thiomethyl-3-cephem-4-carboxylic acid (Compound No. 40).

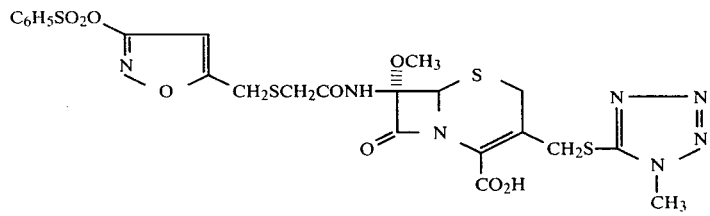

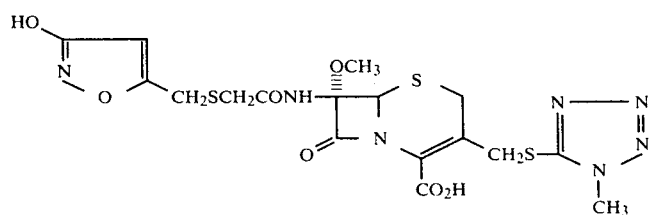

A solution of 70 mg of 7β-[(3-benzenesulphonyloxyisoxazol-5-yl)methylthioacetamido]-7α-methoxy-3-(1-methyl-1H-tetrazol-5-yl)-thiomethyl-3-cephem-4-carboxylic acid (prepared as described in Example 18) in a 5% aqueous solution of sodium hydrogen carbonate was stirred at room temperature for 2 hours. After adjusting the pH of the solution to 2.0 by the addition of 3N hydrochloric acid, the solution was extracted with ethyl acetate. The extract was washed with aqueous sodium chloride and then dried. The solvent was distilled off to give 25 mg (45%) of the desired Compound No. 40.

Infra-red absorption spectrum (Nujol) $\nu$ cm$^{-1}$: 1780 (β-lactam C=O).

Nuclear magnetic resonance spectrum (deuterated acetone) δ ppm: 5.98 (singlet, 1H, 4-isoxazole H); 5.10 (singlet, 1H, 6-cephem H); 4.47 (AB-type quartet, 2H, J=13.0 Hz, 3-cephem CH$_2$); 4.00 (singlet, 3H, CH$_3$ on tetrazole); 3.92 (singlet, 2H, CH$_2$SCH$_2$CO); 3.72 (singlet, 2H, 2-cephem H$_2$); 3.50 (singlet, 3H, 7α-OCH$_3$); 3.40 (singlet, 2H, CH$_2$SCH$_2$CO).

EXAMPLE 20

7β-[(3-Benzoyloxyisoxazol-5-yl)methylsulphonylacetamido]-7α-methoxy-3-(1-methyl-1H-tetrazol-5-yl)thiomethyl-3-cephem-4-carboxylic acid (Compound No. 41).

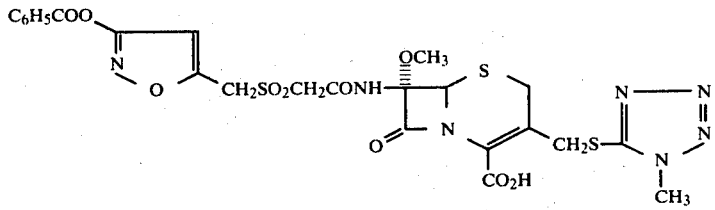

723 mg of (3-benzoyloxyisoxazol-5-yl)methylsulphonylacetic acid were dissolved in 20 ml of methylene chloride; 417 mg of phosphorus pentachloride were added to the solution and the mixture was stirred at room temperature for 1.5 hour, after which the solvent was distilled off under reduced pressure. The resulting (3-benzoyloxyisoxazol-5-yl)methylsulphonylacetyl chloride was dissolved in 15 ml of methylene chloride and this solution was added to a solution of 787 mg of benzhydryl 7β-amino-7α-methoxy-3-(1-methyl-1H-tetrazol-5-yl)thiomethyl-3-cephem-4-carboxylate and 299 mg of N,N-diethylaniline in 15 ml of methylene chloride. The reaction mixture was stirred for 2 hours in an ice bath and then treated as described in Example 19 to give 580 mg (45%) of the benzhydryl ester of the desired Compound No. 41.

580 mg of this ester were dissolved in a mixture of 5 ml of methylene chloride and 0.6 ml of anisole, and then 5 ml of trifluoroacetic acid were added, with ice-cooling, to the solution and stirred for 30 minutes. At the end of this time, the methylene chloride was distilled off under reduced pressure and diisopropyl ether was added to the residue. The precipitates which formed were collected by filtration, and adsorbed on a silica gel preparative thin layer chromatograph and developed by a 8:5:1:1 by volume mixture of chloroform, ethanol, acetic acid and water, to give 322 mg (68.7%) of the desired Compound No. 41.

Infra-red absorption spectrum (Nujol) $\nu$ cm$^{-1}$: 1780 (β-lactam C=O).

Nuclear magnetic resonance spectrum (deuterated acetone) δ ppm: 7.50–8.30 multiplet, 5H, C$_6$H$_5$); 6.92 (singlet, 1H, 4-isoxazole H); 5.10 (singlet, 1H, 6-cephem H); 5.01 (singlet, 2H, CH$_2$SO$_2$CH$_2$CO); 4.38 (singlet, 4H, SO$_2$CH$_2$CO, 3-cephem CH$_2$); 3.94 (singlet, 3H, CH$_3$ on tetrazole); 3.68 (singlet, 2H, 2-cephem H$_2$); 3.52 (singlet, 3H, 7α-OCH$_3$).

EXAMPLE 21

7β-[(3-hydroxyisoxazol-5-yl)methylsulphonylacetamido]-7α-methoxy-3-(1-methyl-1H-tetrazol-5-yl)thiomethyl-3-cephem-4-carboxylic acid (Compound No. 42).

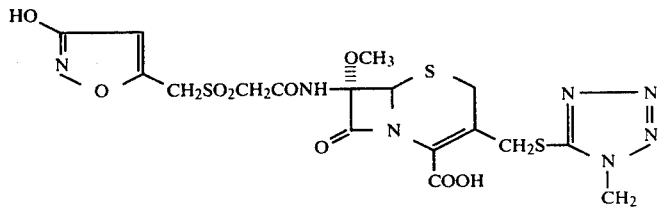

150 mg of 7β-[(3-benzoyloxyisoxazol-5-yl)methylsulphonylacetamido]-7α-methoxy-3-(1-methyl-1H-tetrazol-5-yl)thiomethyl-3-cephem-4-carboxylic acid (prepared as described in Example 20) was treated by the procedure described in Example 19 to give 50 mg (39.1%) of the desired Compound No. 42.

Infra-red absorption spectrum (Nujol) $\nu$cm$^{-1}$: 1777 (β-lactam C=O).

Nuclear magnetic resonance spectrum (CD$_3$OD) δppm: 6.30 (singlet, 1H, 4-isoxazole H); 5.17 (singlet, 1H, 6-cephem H);
4.93 (singlet, 2H, CH$_2$SO$_2$CH$_2$CO); 4.50 (AB-type quartet, 2H, J=14.0 Hz, 3-cephem CH$_2$); 4.34 (singlet, 2H, SO$_2$CH$_2$CO); 4.08 (singlet, 3H, CH$_3$ on tetrazole); 3.72 (singlet, 2H, 2-cephem H$_2$); 3.67 (singlet, 3H, 7α-OCH$_3$).

EXAMPLE 22

7β-[(4-Chloro-3-hydroxyisoxazol-5-yl)methylthioacetamido]-7α-methoxy-3-(1-methyl-1H-tetrazol-5-yl)thiomethyl-3-cephem-4-carboxylic acid (Compound No. 43).

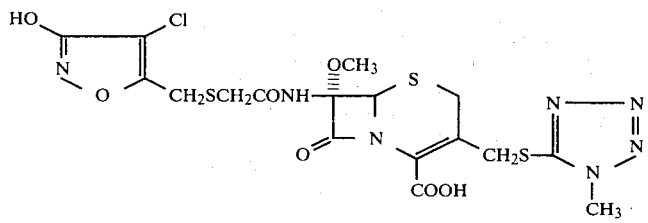

680 mg of (4-chloro-3-mesyloxyisoxazol-5-yl)methylthioacetic acid were dissolved in 20 ml of methylene chloride; 534 mg of phosphorus pentachloride were added to the solution and the mixture was stirred at room temperature for 1 hour, after which the solvent was distilled off under reduced pressure. The resulting (4-chloro-3-mesyloxyisoxazol-5-yl)methylthioacetyl chloride was dissolved in 25 ml of methylene chloride and this solution was added to a solution of 525 mg of benzhydryl 7β-amino-7α-methoxy-3-(1-methyl-1H-tetrazol-5-yl)thiomethyl-3-cephem-4-carboxylate and 383 mg of N,N-diethylaniline in 15 ml of methylene chloride. The reaction mixture was stirred in an ice bath for 1 hour, after which the solvent was distilled off. The residue was dissolved in ethyl acetate and this solution was washed with, in turn, aqueous sodium chloride, aqueous potassium hydrogen sulphate, aqueous sodium chloride, aqueous sodium hydrogen carbonate and aqueous sodium chloride and then dried. The solvent was then distilled off and the residue (1.9 g) was dissolved in a mixture of 4 ml of methylene chloride and 2 ml of anisole, and then 4 ml of trifluoroacetic acid were added to the solution with ice-cooling and the mixture was stirred for 30 minutes. After this, 100 ml of diisopropyl ether were added to the mixture and the precipitates produced were collected by filtration to give 0.94 g of the mesyl ester of the desired compound.

This ester was dissolved in a mixture of 15 ml each of water, methanol and acetone. The pH of the solution was adjusted to 9 by the addition of 1 N aqueous ammonia and then the solution was stirred, under ice-cooling, for 3 hours. The solution was adjusted to a pH of 7 and then the solvent was distilled off under reduced pressure. The pH of the resulting aqueous solution was adjusted to 2 by adding dilute hydrochloric acid and then the solution was extracted with ethyl acetate. The ethyl acetate extract was washed with aqueous sodium chloride and dried and then the solvent was distilled off under reduced pressure. The residue was adsorbed on a silica gel preparative thin layer chromatograph and developed by a 8:5:1:1 by volume mixture of chloroform, methanol, acetic acid and water, to give 285 mg (53.9%) of the desired Compound No. 43.

Infra-red absorption spectrum (Nujol) $\nu$ cm$^{-1}$; 1778 (β-lactam C=O).

Nuclear magnetic resonance spectrum (deuterated acetone)δ ppm: 5.10 (singlet, 1H, 6-cephem H); 4.41 (AB-type quartet, 2H, J=13.5 Hz, 3-cephem CH$_2$); 3.98 (singlet, 5H, CH$_2$SCH$_2$CO, CH$_3$ on tetrazole); 3.69 (singlet, 2H, 2-cephem H$_2$); 3.49 (singlet, 3H, 7α-OCH$_3$); 3.44 (singlet, 2H, SCH$_2$CO).

EXAMPLE 23

7β-[(4-Chloro-3-hydroxyisoxazol-5-yl)methylsulphonylacetamido]-7α-methoxy-3-(1-methyl-1H-tetrazol-5-yl)thiomethyl-3-cephem-4-carboxylic acid (Compound No. 44).

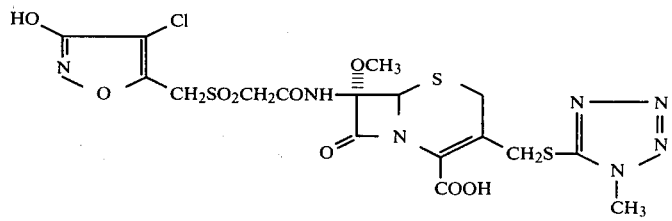

468 mg of (4-chloro-3-mesyloxyisoxazol-5-yl)methylsulphonylacetic acid were dissolved in 15 ml of methylene chloride; 292 mg of phosphorus pentachloride were added to the solution and the mixture was stirred under ice-cooling for 1.5 hours, after which the solvent was distilled off under reduced pressure. The resulting (4-chloro-3-mesyloxyisoxazol-5-yl)methylsulphonylacetyl chloride was dissolved in 20 ml of methylene chloride and this solution was added to a solution of 350 mg of benzhydryl 7β-amino-7α-methoxy-3-(1-methyl-1H-tetrazol-5-yl)thiomethyl-3-cephem-4-carboxylate and 209 mg of N,N-diethylaniline in 10 ml of methylene chloride. The reaction mixture was stirred in an ice bath for 1 hour, and then the solvent was distilled off. The residue was dissolved in ethyl acetate and the resulting solution was washed with aqueous sodium chloride and dried, after which the solvent was distilled off. The residue (700 mg) was dissolved in a mixture of 2 ml of methylene chloride and 1 ml of anisole, and then 2 ml of trifluoroacetic acid were added to the solution under ice-cooling and the mixture was stirred for 1 hour. After this, 50 ml of diisopropyl ether were added and the precipitates produced were collected by filtration to give 400 mg (70%) of the mesyl ester of the desired Compound No. 44.

This ester was dissolved in a mixture of 5 ml of acetone and 5 ml of water and treated with 1 N aqueous ammonia as described in Example 22; the product was then purified by silica gel thin layer chromatography to give 167 mg (48%) of the desired Compound No. 44.

Infra-red absorption spectrum (Nujol) ν cm¹: 1777 (β-lactam C=O).

Nuclear magnetic resonance spectrum (deuterated acetone)δppm:

5.09 (singlet, 1H, 6-cephem H); 4.88 (singlet, 2H, CH$_2$SO$_2$CH$_2$CO); 4.34 (singlet, 4H, SO$_2$CH$_2$CO, 3-cephem CH$_2$); 3.95 (singlet, 3H, CH$_3$ on tetrazole); 3.66 (singlet, 2H, 2-cephem H$_2$); 3.48 (singlet, 3H, 7α-OCH$_3$).

EXAMPLE 24

Pharmaceutical Preparation

Sterile sodium 7β-[(3-mesyloxyisoxazol-5-yl)acetamido]-7α-methoxy-3-(1-methyl-1H-tetrazol-5-yl)thiomethyl-3-cephem-4-carboxylate was divided, under sterile conditions, into sterile vials, so that each contained 250 mg of the compound. The vials were lyophilized and sealed aseptically. For use, 2 ml of water for injections can be added to each vial.

EXAMPLE 25

Pharmaceutical Preparation

Sterile sodium 7β-[(3-hydroxy-4-methoxycarbonylisoxazol-5-yl)acetamido]-7α-methoxy-3-(1-methyl-1H-tetrazol-5-yl)thiomethyl-3-cephem-4-carboxylate was divided, under sterile conditions, into sterile vials so that each contained 250 mg of the compound. The vials were lyophilized and sealed aseptically. For use, 2 ml of water for injections can be added to each vial.

EXAMPLE 26

Pharmaceutical Preparation

Sterile sodium 7β-[(4-chloro-3-hydroxyisoxazol-5-yl)-methylsulphonylacetamido]-7α-methoxy-3-(1-methyl-1H-tetrazol-5-yl)-thiomethyl-3-cephem-4-carboxylate was divided, under sterile conditions, into sterile vials, so that each contained 250 mg of the compound. The vials were lyophilized and sealed aseptically. For use, 2 ml of water for injections can be added to each vial.

We claim:

1. 7α-Methoxycephalosporin derivatives of general formula (I):

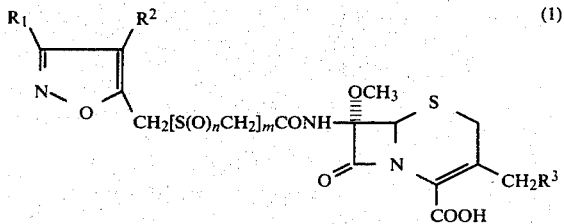

wherein:

R$^1$ represents: a hydroxy group; a C$_1$-C$_4$ alkoxy group; a C$_2$-C$_5$ aliphatic acyloxy group; a benzoyloxy group which is unsubstituted or has one or more C$_1$-C$_4$ alkyl, C$_1$-C$_4$ alkoxy, nitro or halogen substituents; a benzenesulphonyloxy group which is unsubstituted or has one or more C$_1$-C$_4$ alkyl substituents; or a C$_1$-C$_3$ alkanesulphonyloxy group which is unsubstituted or has one or more C$_1$-C$_3$ alkoxy, cyano, nitro, halogen or C$_2$-C$_4$ alkoxycarbonyl substituents;

R$^2$ represents a hydrogen atom; a C$_1$-C$_4$ alkyl group; a halogen atom; a carboxyl group; a C$_2$-C$_5$ alkoxycarbonyl group; a carbamoyl group; a (C$_1$-C$_3$ alkyl)-substituted carbamoyl group; a di(C$_1$-C$_3$ alkyl)carbamoyl group; or a cyano group;

R$^3$ represents a hydrogen atom; an acetoxy group; a carbamoyloxy group; or a tetrazolylthio, thiadiazolylthio or oxadiazolylthio group which is unsubstituted or has one or more C$_1$-C$_3$ alkyl, sulphomethyl or di(C$_1$ or C$_2$ alkyl)amino(C$_1$-C$_3$ alkyl) substituents m is 0 or 1; and n is 0 or 2;

and pharmaceutically acceptable salts and esters thereof.

2. Compounds as claimed in claim 1, wherein:

R$^1$ represents a hydroxy group, an unsubstituted benzoyloxy group or a methanesulphonyloxy group;

R$^2$ represents a hydrogen atom, a C$_1$-C$_3$ alkyl group, a halogen atom, a C$_2$-C$_4$ alkoxycarbonyl group, a carbamoyl group, a (C$_1$-C$_3$ alkyl)-substituted carbamoyl group, a di(C$_1$-C$_3$ alkyl)carbamoyl group or a cyano group;

R$^3$ represents a (C$_1$-C$_3$ alkyl)-substituted tetrazolylthio group;

m is 0 or 1; and when m=1, n=2.

3. Compounds as claimed in claim 1, wherein:

R$^1$ represents a hydroxy group, an unsubstituted benzoyloxy group or a methanesulphonyloxy group;

R$^2$ represents a hydrogen atom, a halogen atom or a C$_2$-C$_4$ alkoxycarbonyl group;

R$^3$ represents a methyl- substituted tetrazolylthio group;

m=0 or 1; and when m=1, n=2.

4. 7β-[(3-Benzoyloxyisoxazol-5-yl)acetamido]-7α-methoxy-3-(1-methyl-1H-tetrazol-5-yl)thiomethyl-3-cephem-4-carboxylic acid.

5. 7β-[(3-Hydroxyisoxazol-5-yl)acetamido]-7α-methoxy-3-(1-methyl-1H-tetrazol-5-yl)thiomethyl-3-cephem-4-carboxylic acid.

6. 7β-[(4-Bromo-3-hydroxyisoxazol-5-yl)acetamido]-7α-methoxy-3-(1-methyl-1H-tetrazol-5-yl)thiomethyl-3-cephem-4-carboxylic acid.

7. 7β-[(4-Chloro-3-hydroxyisoxazol-5-yl)acetamido]-7α-methoxy-3-(1-methyl-1H-tetrazol-5-yl)thiomethyl-3-cephem-4-carboxylic acid.

8. 7β-[(3-Mesyloxyisoxazol-5-yl)acetamido]-7α-methoxy-3-(1-methyl-1H-tetrazol-5-yl)thiomethyl-3-cephem-4-carboxylic acid.

9. 7β-[(4-Chloro-3-mesyloxyisoxazol-5-yl)acetamido]-7α-methoxy-3-(1-methyl-1H-tetrazol-5-yl)thiomethyl-3-cephem-4-carboxylic acid.

10. 7β-[(4-Bromo-3-mesyloxyisoxazol-5-yl)acetamido]-7α-methoxy-3-(1-methyl-1H-tetrazol-5-yl)thiomethyl-3-cephem-4-carboxylic acid.

11. 7β-[(3-Hydroxy-4-methoxycarbonylisoxazol-5-yl)acetamido]7α-methoxy-3-(1-methyl-1H-tetrazol-5-yl)thiomethyl-3-cephem-4-carboxylic acid.

12. 7β-[(3-Benzoyloxyisoxazol-5-yl)methylsulphonylacetamido]-7α-methoxy-3-(1-methyl-1H-tetrazol-5-yl)thiomethyl-3-cephem-4-carboxylic acid.

13. 7β-[(3-Hydroxyisoxazol-5-yl)methylsulphonylacetamido]-7α-methoxy-3-(1-methyl-1H-tetrazol-5-yl)thiomethyl-3-cephem-4-carboxylic acid.

14. 7α-Methoxycephalosporin derivatives of formula (II):

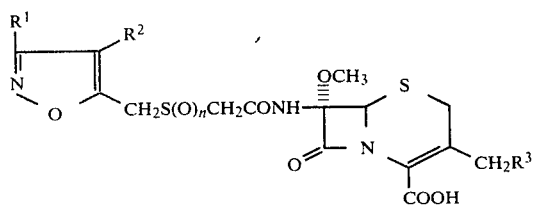

(II)

wherein:
- $R^1$ represents: a hydroxy group; a $C_1$–$C_4$ alkoxy group; a $C_2$–$C_5$ aliphatic acyloxy group; a benzoyloxy group which is unsubstituted or has one or more $C_1$–$C_4$ alkyl, $C_1$–$C_4$ alkoxy, nitrogen or halogen substituents; a benzenesulphonyloxy group which is unsubstituted or has one or more $C_1$–$C_4$ alkyl substituents; or a $C_1$–$C_3$ alkanesulphonyloxy group which is unsubstituted or has one or more $C_1$–$C_3$ alkoxy, cyano, nitro, halogen or $C_2$–$C_4$ alkoxycarbonyl substituents;
- $R^2$ represents a hydrogen atom; a $C_1$–$C_4$ alkyl group; a halogen atom; a carboxyl group; a $C_2$–$C_5$ alkoxycarbonyl group; a carbamoyl group; a ($C_1$–$C_3$ alkyl)-substituted carbamoyl group; a di($C_1$–$C_3$ alkyl)carbamoyl group; or a cyano group;
- $R^3$ represents a hydrogen atom; an acetoxy group; a carbamoyloxy group; or a tetrazolylthio, thiadiazolylthio or oxadiazolylthio group which is unsubstituted or has one or more $C_1$–$C_3$ alkyl, sulphomethyl or di($C_1$ or $C_2$ alkyl)amino($C_1$–$C_3$ alkyl) substituents and
- n is 0 or 2;

and pharmaceutically acceptable salts and esters thereof.

15. 7α-Methoxycephalosporin derivatives of formula (III):

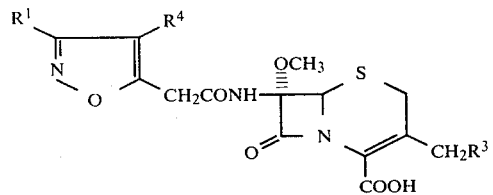

(III)

wherein:
- $R^1$ represents: a hydroxy group; a $C_1$–$C_4$ alkoxy group; a $C_2$–$C_5$ aliphatic acyloxy group; a benzoyloxy group which is unsubstituted or has one or more $C_1$–$C_4$ alkyl, $C_1$–$C_4$ alkoxy, nitro or halogen substituents; a benzenesulphonyloxy group which is unsubstituted or has one or more $C_1$–$C_4$ alkyl substituents; or a $C_1$–$C_3$ alkanesulphonyloxy group which is unsubstituted or has one or more $C_1$–$C_3$ alkoxy, cyano, nitro, halogen or $C_2$–$C_4$ alkoxycarbonyl substituents;
- $R^3$ represents a hydrogen atom; an acetoxy group; a carbamoyloxy group; or a tetrazolylthio, thiadiazolylthio or oxadiazolylthio group which is unsubstituted or has one or more $C_1$–$C_3$ alkyl, sulphomethyl or di($C_1$ or $C_2$ alkyl)amino($C_1$–$C_3$ alkyl) substituents; and
- $R^4$ represents a hydrogen atom, a $C_1$–$C_4$ alkyl group or a halogen atom;

and pharmaceutically acceptable salts and esters thereof.

16. A pharmaceutical composition having antibacterial activity comprising a pharmaceutically acceptable carrier or diluent and, as active ingredient, a 7α-methoxycephalosporin derivative of general formula (I):

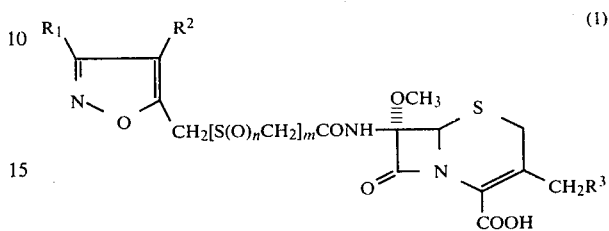

(I)

wherein:
- $R^1$ represents: a hydroxy group; a $C_1$–$C_4$ alkoxy group; a $C_2$–$C_5$ aliphatic acyloxy group; a benzoyloxy group which is unsubstituted or has one or more $C_1$–$C_4$ alkyl, $C_1$–$C_4$ alkoxy, nitro or halogen substituents; a benzenesulphonyloxy group which is unsubstituted or has one or more $C_1$–$C_4$ alkyl substituents; or a $C_1$–$C_3$ alkanesulphonyloxy group which is unsubstituted or has one or more $C_1$–$C_3$ alkoxy, cyano, nitro, halogen or $C_2$–$C_4$ alkoxycarbonyl substituents;
- $R^2$ represents a hydrogen atom; a $C_1$–$C_4$ alkyl group; a halogen atom; a carboxyl group; a $C_2$–$C_5$ alkoxycarbonyl group; a carbamoyl group; a ($C_1$–$C_3$ alkyl)-substituted carbamoyl group; a di($C_1$–$C_3$ alkyl)carbamoyl group; or a cyano group;
- $R^3$ represents a hydrogen atom; an acetoxy group; a carbamoyloxy group; or a tetrazolylthio, thiadiazolylthio or oxadiazolylthio group which is unsubstituted or has one or more $C_1$–$C_3$ alkyl, sulphomethyl or di($C_1$ or $C_2$ alkyl)amino($C_1$–$C_3$ alkyl)substituents;
- m is 0 or 1; and
- n is 0 or 2;

or a pharmaceutically acceptable salt or ester thereof.

17. A pharmaceutical composition as claimed in claim 16, wherein said 7α-methoxycephalosporin derivative is selected from the group consisting of:
- 7β-[(3-Benzoyloxyisoxazol-5-yl)acetamido]-7α-methoxy-3-(1-methyl-1H-tetrazol-5-yl)thiomethyl-3-cephem-4-carboxylic acid;
- 7β-[(3-Hydroxyisoxazol-5-yl)acetamido]-7α-methoxy-3-(1-methyl-1H-tetrazol-5-yl)thiomethyl-3-cephem-4-carboxylic acid;
- 7β-[(4-Bromo-3-hydroxyisoxazol-5-yl)acetamido]-7α-methoxy-3-(1-methyl-1H-tetrazol-5-yl)thiomethyl-3-cephem-4-carboxylic acid;
- 7β-[(4-Chloro-3-hydroxyisoxazol-5-yl)acetamido]-7α-methoxy-3-(1-methyl-1H-tetrazol-5-yl)thiomethyl-3-cephem-4-carboxylic acid;
- 7β-[(3-Mesyloxyisoxazol-5-yl)acetamido]-7α-methoxy-3-(1-methyl-1H-tetrazol-5-yl)thiomethyl-3-cephem-4-carboxylic acid;
- 7β-[(4-Chloro-3-mesyloxyisoxazol-5-yl)acetamido]-7α-methoxy-3-(1-methyl-1H-tetrazol-5-yl)thiomethyl-3-cephem-4-carboxylic acid;
- 7β-[(4-Bromo-3-mesyloxyisoxazol-5-yl)acetamido]-7α-methoxy-3-(1-methyl-1H-tetrazol-5-yl)thiomethyl-3-cephem-4-carboxylic acid;

7β-[(3-Hydroxy-4-methoxycarbonylisoxazol-5-yl)acetamido]7α-methoxy-3-(1-methyl-1H-tetrazol-5-yl)thiomethyl-3-cephem-4-carboxylic acid;

7β-[(3-Benzoyloxyisoxazol-5-yl)methylsulphonylacetamido]7α-methoxy-3-(1-methyl-1H-tetrazol-5-yl)thiomethyl-3-cephem-4-carboxylic acid; and 7β-[(3-Hydroxyisoxazol-5-yl)methylsulphonylacetamido]7α-methoxy-3-(1-methyl-1H-tetrazol-5-yl)thiomethyl-3-cephem-4-carboxylic acid.

* * * * *